(12) United States Patent
Inoue et al.

(10) Patent No.: US 10,612,021 B2
(45) Date of Patent: Apr. 7, 2020

(54) THERAPEUTIC OR PROPHYLACTIC COMPOSITION FOR TDP-43 PROTEINOPATHY

(71) Applicant: KYOTO UNIVERSITY, Kyoto (JP)

(72) Inventors: Haruhisa Inoue, Kyoto (JP); Itaru Tsuge, Kyoto (JP); Koh Ono, Kyoto (JP); Shigehiko Suzuki, Kyoto (JP); Motoko Naitoh, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/370,032

(22) Filed: Dec. 6, 2016

(65) Prior Publication Data

US 2017/0226508 A1    Aug. 10, 2017

(30) Foreign Application Priority Data

Oct. 7, 2015  (JP) .................................. 2015-199526

(51) Int. Cl.
   *C12N 15/113* (2010.01)

(52) U.S. Cl.
   CPC ...... *C12N 15/113* (2013.01); *C12N 2310/141* (2013.01); *C12N 2310/20* (2017.05); *C12N 2320/32* (2013.01)

(58) Field of Classification Search
   CPC .......................... C12N 15/113; C12N 2310/141
   See application file for complete search history.

(56) References Cited

U.S. PATENT DOCUMENTS

| | | | |
|---|---|---|---|
| 8,563,708 B2 * | 10/2013 | Brown ................... | C12N 15/111 536/24.1 |
| 2010/0004320 A1 | 1/2010 | Elmen | |
| 2010/0286234 A1 | 11/2010 | Elmen | |
| 2012/0053229 A1 | 3/2012 | Naar | |
| 2012/0083596 A1 | 4/2012 | Elmen | |
| 2012/0238618 A1 | 9/2012 | Elmen | |
| 2013/0150431 A1 * | 6/2013 | Fernandez-Hernando ................... A61K 31/713 514/44 A |
| 2014/0288158 A1 * | 9/2014 | Rajeev ................. | C12N 15/113 514/44 A |
| 2014/0329883 A1 | 11/2014 | Elmen | |
| 2015/0045330 A1 | 2/2015 | Egawa | |
| 2015/0247143 A1 * | 9/2015 | Fitzgerald ............ | C12N 15/113 514/44 A |
| 2016/0060627 A1 | 3/2016 | Elmen | |

FOREIGN PATENT DOCUMENTS

| | | |
|---|---|---|
| JP | 2012-522509 | 9/2012 |
| JP | 5149528 A2 | 2/2013 |
| JP | 5198430 A2 | 5/2013 |
| JP | 2015-506905 | 3/2015 |
| WO | WO2008/061537 | * 5/2008 |

OTHER PUBLICATIONS

Huang et al. BMC Genomics 212 13:159, pp. 1-10 (Year: 2012).*
Huang et al. BMC Genomics 212 13:159, table 1 pp. 1-3 (Year: 2012).*
Emma L. Scotter et al: "TDP-43 Proteinopathy and ALS: Insights into Disease Mechanisms and Therapeutic Targets", Neurotherapeutics, Feb. 5, 2015, 12, pp. 352-363, cited in specification.
Iga Wegorzewska et al: "TDP-43 mutant transgenic mice develop features of ALS and frontotemporal lobar degeneration", Proceedings of the National Academy of Sciences of the United States of America, Nov. 3, 2009, vol. 106, No. 44, pp. 18809-18814, cited in specification.
Vivek Swarup et al: "Pathological hallmarks of amyotrophic lateral sclerosis/frontotemporal lobar degeneration in transgenic mice produced with TDP-43 genomic fragments", A Journal of Neurology, Jul. 13, 2011, 134, pp. 2610-2626, cited in specification.
English Abstract only of Kasai T et al: "Increased TDP-43 protein in cerebrospinal fluid of patients with amyotrophic lateral sclerosis", Acta Neuropathol, Jan. 2009, 117(1), 55-62, cited in specification.
Chen Wenqiang et al: "Pakin-mediated reduction of nuclear and soluble TDP-43 reverses behavioral decline in symptomatic mice", Human Molecular Genetics, May 8, 2014, vol. 23, No. 18, pp. 4960-4969, cited in specification.
Quan Li et al: "The cleavage pattern of TDP-43 determines its rate of clearance and cytotoxicity", Nature Communications, Jan. 29, 2015, 6:6183, pp. 1-12, cited in specification.
English Abstract only of Egawa N et al: "Drug screening for ALS using patient-specific induced pluripotent stem cells", Science Translational Medicine, Aug. 1, 2012, 4(145), 145ra104, cited in specification.
Youhna M Ayala et al: "TDP-43 regulates its mRNA levels through a negative feedback loop", The European Molecular Biology Organization Journal, 2011, vol. 30, No. 2, pp. 277-288.

* cited by examiner

Primary Examiner — Brian Whiteman
(74) Attorney, Agent, or Firm — Rankin, Hill & Clark LLP

(57) ABSTRACT

The present invention aims to provide a composition for the prevention or treatment of TDP-43 proteinopathy using a microRNA targeting the TDP-43 gene.
A prophylactic or therapeutic composition for TDP-43 proteinopathy, comprising: one or more nucleic adds selected from the group consisting of isolated RNAs and isolated nucleic acids encoding the RNAs, wherein the RNAs consist of human miR-33 represented by SEQ ID NO: 1, variants of the human miR-33 having one or more mutations, and precursors of the human miR-33 and the variants.

9 Claims, 19 Drawing Sheets

Specification includes a Sequence Listing.

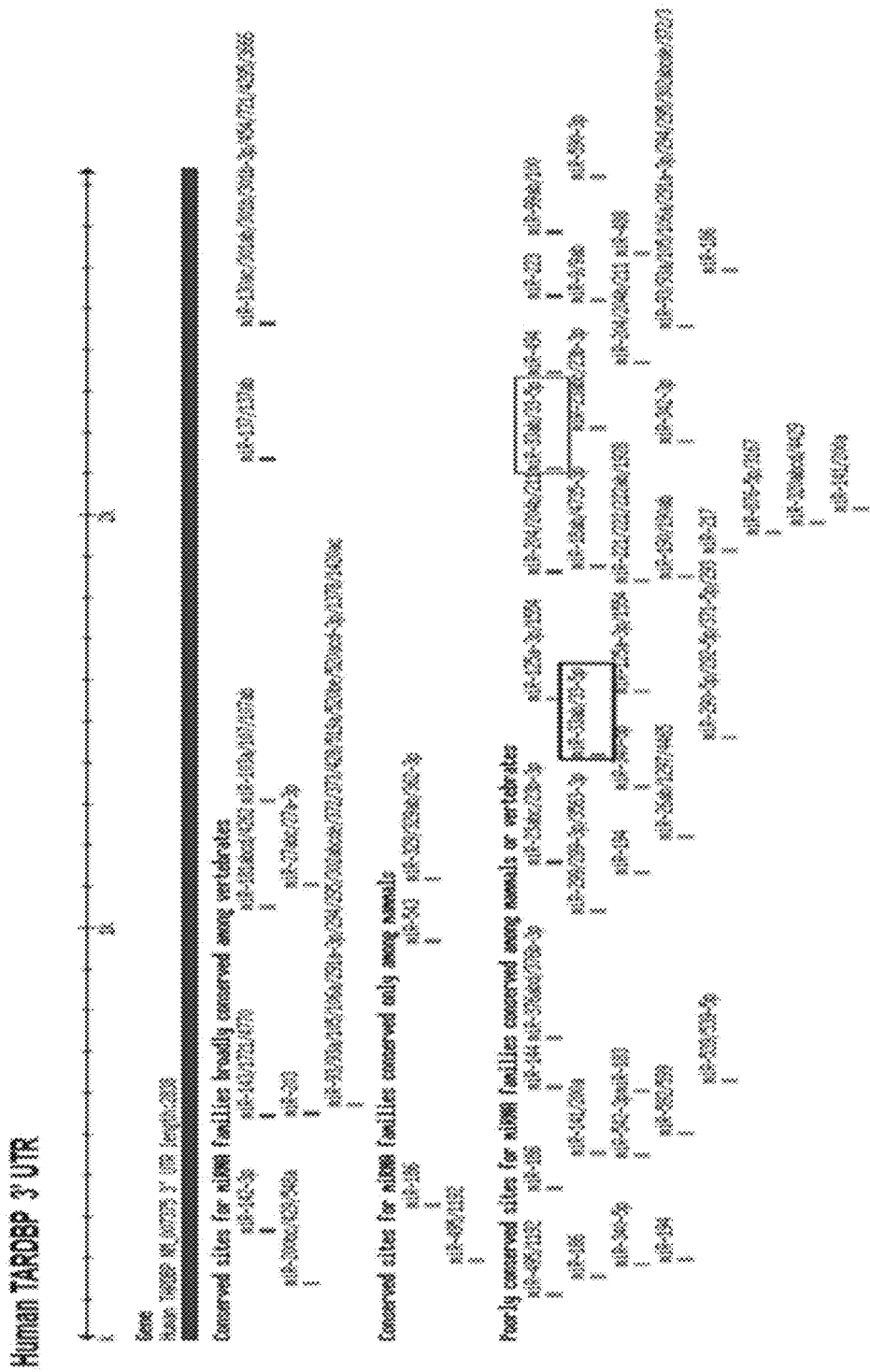

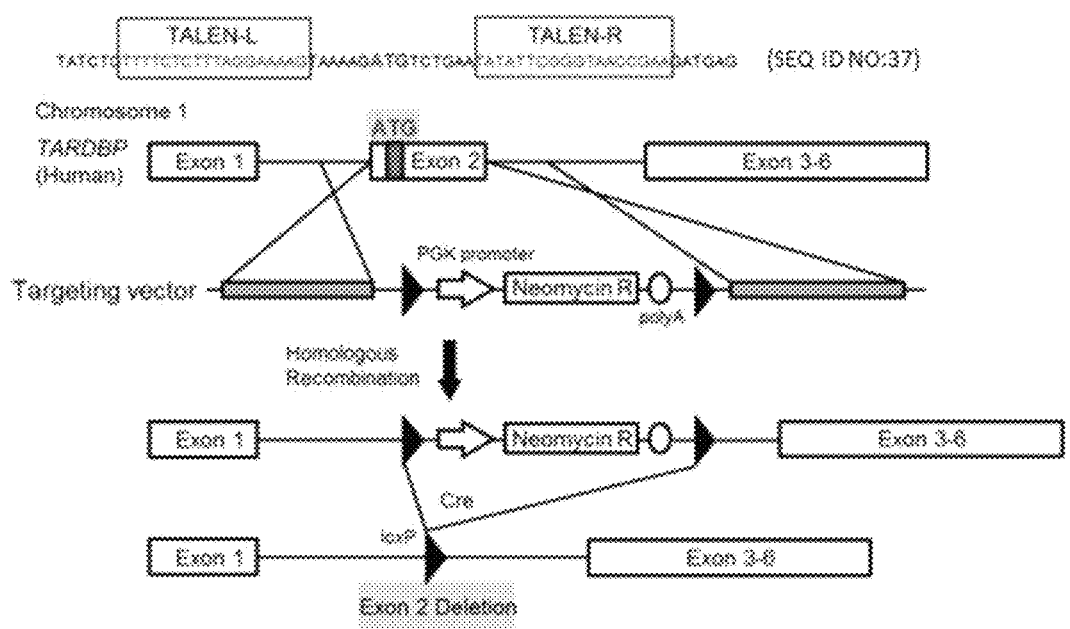

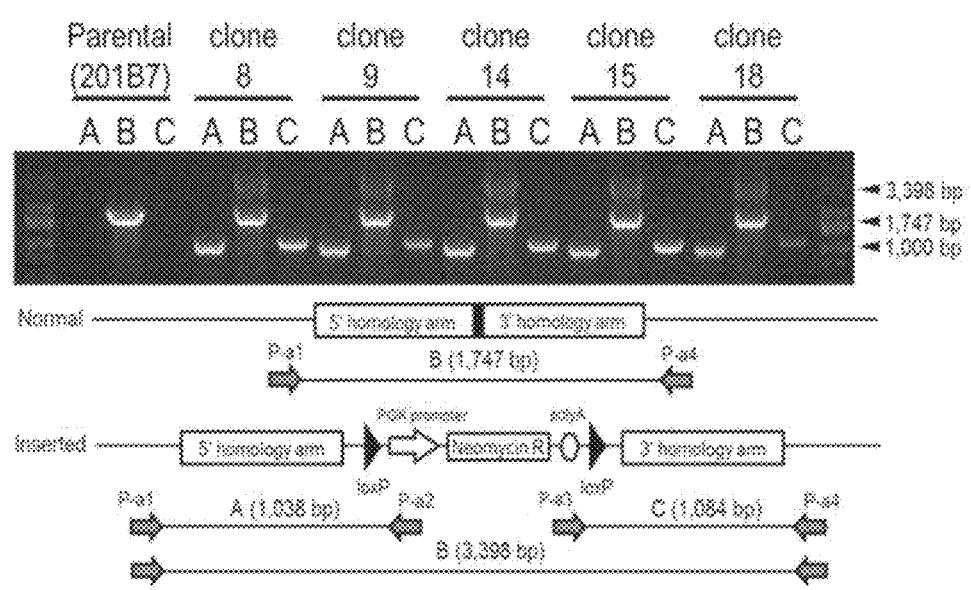

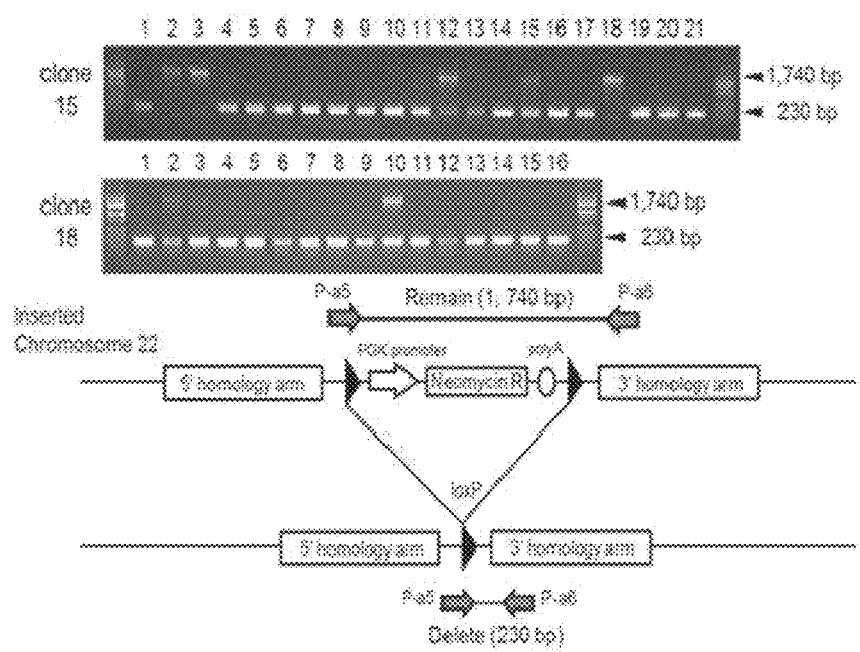

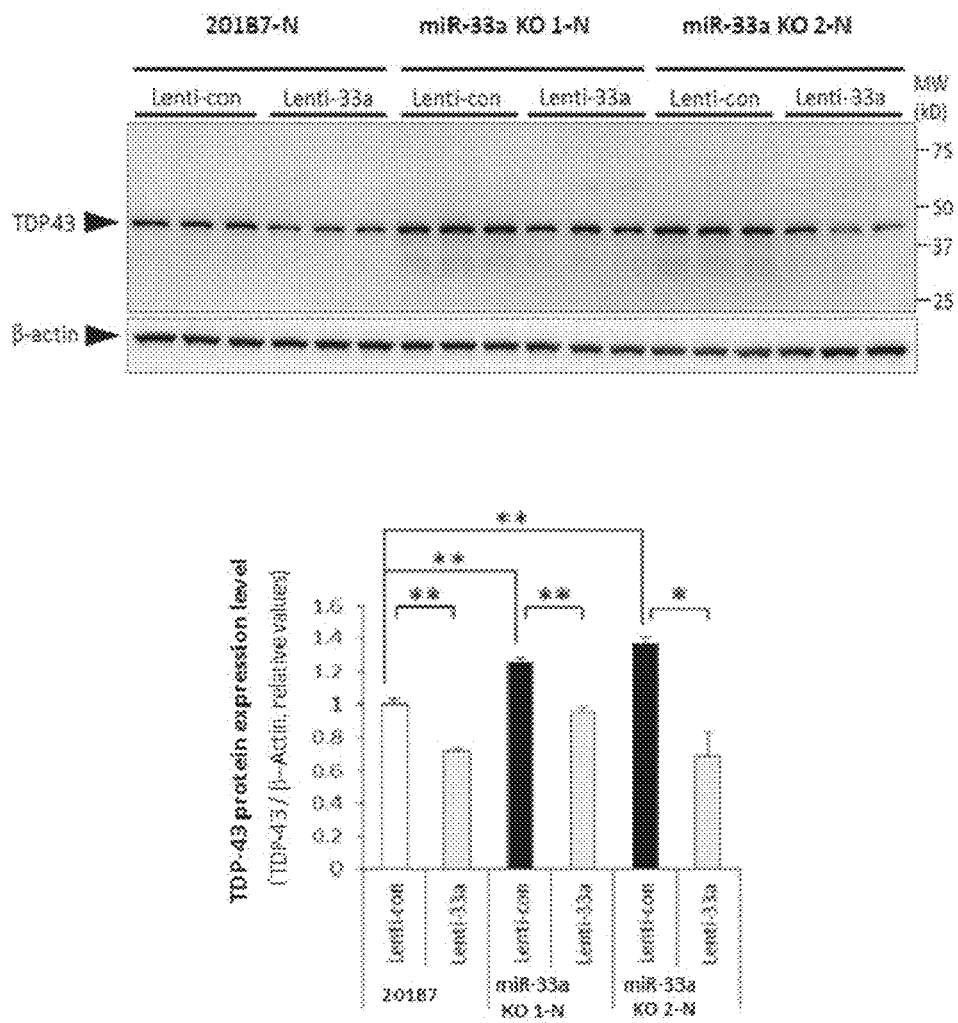

THERAPEUTIC OR PROPHYLACTIC COMPOSITION FOR TDP-43 PROTEINOPATHY

TECHNICAL FIELD

The present invention relates to a prophylactic or therapeutic composition for TDP-43 proteinopathy (TDP-43 proteinopathy). More specifically, the present invention relates to the said composition using a microRNA targeting the TDP-43 gene.

BACKGROUND ART

TDP-43 (TAR-DNA-binding protein of 43 kDa, Official Symbol; TARDBP, NM_007375, NP_031401) is a DNA/RNA-binding protein expressed in almost all types of cells. This protein is predominantly localized in nuclei and known to regulate splicing reaction of RNAs and also participate in the formation of certain microRNAs. Moreover, some of the TDP-43 proteins are known to be transported to cytoplasm and function as carriers for a local transport of RNAs within a cell (Non-Patent Document 1).

TDP-43 has been one of the most noteworthy proteins in the field of neurodegenerative diseases since TDP-43 was found to be a principal component of ubiquitin-positive intracellular inclusions appearing in a lesion site-specific manner in frontotemporal lobar degeneration with ubiquitin inclusions (FTLD-U) and amyotrophic lateral sclerosis (ALS) in 2006. FTLD is progressive dementia caused by neurodegeneration of the frontal lobe and/or the temporal lobe. ALS is a progressive motor neuron disease caused by selective degeneration of upper and/or lower motor neurons. The finding of TDP-43 in both FTLD-U and ALS suggests a possibility that these two neurodegenerative diseases, which differ in degeneration site and symptom, share a common mechanism of pathogenesis.

The TDP-43 proteins within the inclusions are aggregated resulting from an abnormal phosphorylation and ubiquitination, and various cytotoxicities are known to occur during the process for aggregation. Cells having the inclusions lack the TDP-43 protein in the nuclei, suggesting that a loss of function of TDP-43 also contributes to the pathogenesis of these diseases.

Accordingly, neurodegenerative diseases accompanying a disappearance of TDP-43 protein from the nuclei and an aggregation thereof in the cytoplasm are categorized as TDP-43 proteinopathy (Non-Patent Document 1).

Thereafter, ALS families having TDP-43 gene mutations were found, and it has been shown that the overexpression of such variant TDP-43 in a mouse nervous system induces neurodegeneration (Non-Patent Document 2). Furthermore, in transgenic mice into which a genomic fragment of human wild-type TDP-43 gene had been introduced, TDP-43 was aggregated in particular neurons and a decline in cognitive functions and impaired motor functions were induced, even though the expression level of TDP-43 was increased in all types of cells (Non-Patent Document 3).

In short, it has been shown that not only the mutant TDP-43 proteins but also the wild-type TDP-43 protein can cause ALS- or FTLD-like pathological conditions when expressed at excessive levels.

It has been further revealed that the concentration of TDP-43 protein in the cerebrospinal fluid of sporadic ALS patients is significantly higher than that of healthy individuals in general (Non-Patent Document 4). There is also a report about increased TDP-43 mRNA levels in autopsied spinal cord tissues of sporadic ALS patients (Non-Patent Document 5).

From these findings, the overexpression of TDP-43 protein is considered to be a primary cause of TDP-43 proteinopathy. In order to treat this disease, energetic studies have been made on methods for correcting the overexpression of TDP-43 protein.

Non-Patent Document 5 has reported that bosutinib and nilotinib approved by the Food and Drug Administration (FDA) as therapeutic drugs for chronic myelocytic leukemia suppress neurodegeneration in transgenic mice overexpressing TDP-43 and ameliorate cognitive functions and motor functions. These drugs are known as blood-brain barrier-permeable tyrosine kinase inhibitors and considered to exert these effects by promoting the clearance of the TDP-43 protein via ubiquitin ligase Parkin.

Non-Patent Document 6 has reported that the clearance of TDP-43 is started when caspase 4, which is a cysteine protease localized on the endoplasmic reticulum membrane, performs cleavage between amino acids at positions 174 and 175 of the TDP-43 protein.

However, these methods are to decrease the amount of the TDP-43 protein in cells by promoting the degradation of the TDP-43 protein. Taking into consideration the fact that the TDP-43 protein itself is cytotoxic in TDP-43 proteinopathy, a method capable of suppressing the production of the TDP-43 protein is expected to produce higher therapeutic effects.

From this point of view, the present inventors established an iPSC (induced pluripotent stem cell) line from ALS patients having TDP-43 gene mutations and established a drug screening system using motor neurons generated from the iPSC by inducing the differentiation (ALS-MN). The ALS-MN is an excellent cell model of the disease that possesses various features (such as poor neurite outgrowth, high vulnerability to stress, and formation of TDP-43-positive aggregates) found in the motor neurons of ALS patients. The present inventors investigated drugs involved in RNA metabolism using this screening system and found that anacardic acid, known as a noncompetitive inhibitor of HAT (histone acetyltransferase), has activities of decreasing a level of TDP-43 mRNA and ameliorating the pathological properties (Patent Document 1, Non-Patent Document 7).

Meanwhile, methods using low-molecular nucleic acids such as antisense oligonucleotides, siRNAs, or microRNAs are known as methods for suppressing certain gene expression specifically. Particularly, microRNAs are greatly expected as drugs since they are endogenous molecules and less likely to cause immune response.

A microRNA forms a miRNA-RISC complex and binds to 3'UTR of a particular mRNA, and causes the degradation or translational inhibition of the mRNA, leading to suppression of its expression. A large number of microRNAs targeting genes involved in various diseases have been identified so far, and drugs containing the microRNAs or low-molecular nucleic acids targeting the microRNAs (anti-miRs) as active ingredients have been developed (e.g., Patent Documents 2 to 4).

However, a microRNA targeting TDP-43 has not yet been reported. Although a large number of microRNAs whose expression varies in TDP-43 proteinopathy have been identified, a microRNA capable of directly regulating the expression of TDP-43 still remains to be discovered.

The TDP-43 protein is known to bind directly to 3'UTR of its own mRNA to promote its degradation as well as a typical microRNA (Non-Patent Document 8). Accordingly, as for TDP-43 gene, a possibility is suggested that the TDP-43 protein itself, instead of microRNAs, regulates its mRNA and protein levels. In addition, it is concerned that a TDP-43-targeting microRNA, if any, might not sufficiently function in cells in which TDP-43 protein has been already overexpressed.

Under these circumstances, developing a method for treating TDP-43 proteinopathy using a microRNA has been considered to be difficult.

PRIOR ART DOCUMENTS

Patent Documents

[Patent Document 1] Japanese Unexamined Patent Application Publication (Translation of PCT Application) No. 2015-506905
[Patent Document 2] Japanese Patent Publication No. 5198430
[Patent Document 3] Japanese Patent Publication No. 5149528
[Patent Document 4] Japanese Unexamined Patent Application Publication (Translation of PCT Application) No. 2012-522509

Non-Patent Documents

[Non-Patent Document 1] Scotter E. L., et al, Neurotherapeutics, 12:352-363, 2015
[Non-Patent Document 2] Wegorzewska I., et al, Proc. Natl. Acad. Sci. USA, 106:18809-18814, 2009
[Non-Patent Document 3] Swarup V., et al, Brain, 134:2610-2626, 2011
[Non-Patent Document 4] Kasai T., et al, Acta. Neuropathol. 117:55-62, 2009
[Non-Patent Document 5] Wenqiang C., et al, Hum. Mol. Genet., 23:4960-4969, 2014
[Non-Patent Document 6] Li Q., et al, Nat. Commun., 6:6183, 2015
[Non-Patent Document 7] Egawa N., et al, Science Translational Medicine, 4:145ra104, 2012
[Non-Patent Document 8] Swarup V., et al, EMBO J., 30:277-288, 2010

SUMMARY OF INVENTION

Technical Problem

The present invention was made in view of the above-described problem of the conventional art and aims to provide a composition for the prevention or treatment of TDP-43 proteinopathy using a microRNA targeting the TDP-43 gene.

Solution to Problem

In order to achieve the above-described object, the present inventors have analyzed the 3'UTR sequence of human TDP-43 gene using a public microRNA target prediction program and found that miR-33 (=miR-33a and miR-33b), which was predicted to have a low possibility of targeting the human TDP-43 3'UTR, is a microRNA targeting the TDP-43 gene. Surprisingly, it has been revealed that TDP-43 is a modulator that negatively regulates the expression of miR-33a in human neurons and the expression level of miR-33a is significantly decreased in iPSC derived from TDP-43 proteinopathy patients. It has been further revealed that, in human motor neurons functionally lacking the miR-33a gene (motor neurons differentiated from miR-33a-knockout iPSC), the neurites become vulnerable due to the elevated expression of TDP-43 and this vulnerability can be recovered by the supply of miR-33a.

Specifically, it has been found that in human neurons, the expression levels of miR-33 and TDP-43 are balanced upon their mutual suppressive effects and, when miR-33 is supplied to neurons that have become vulnerable due to the overexpression of TDP-43 by lacking this balance, this overexpression is corrected and the vulnerability is ameliorated. On the basis of these findings, the present invention has been completed.

That is, the present invention provides the following.

[1] A prophylactic or therapeutic composition for TDP-43 proteinopathy, including one or more nucleic acids selected from the group consisting of isolated RNAs of human miR-33 represented by SEQ ID NO: 1, isolated RNAs of variants of the human miR-33, isolated RNAs of precursors of the human miR-33 and the variants, and isolated nucleic acids encoding the RNAs.
[2] The prophylactic or therapeutic composition for TDP-43 proteinopathy according to [1], wherein the mutation site is a base at position 1, or one or more bases at or subsequent to position 9 from the 5' end of the human miR-33.
[3] The prophylactic or therapeutic composition for TDP-43 proteinopathy according to [1] or [2], wherein the mutation is a substitution, a deletion, or an insertion of 5 or less nucleotides.
[4] The prophylactic or therapeutic composition for TDP-43 proteinopathy according to any of [1] to [3], wherein the precursors are double-stranded miRNAs and/or pre-miRNAs.
[5] The prophylactic or therapeutic composition for TDP-43 proteinopathy according to any of [1] to [4], wherein the isolated nucleic acids encoding the RNAs are functionally encoded by a virus vector.
[6] The prophylactic or therapeutic composition for TDP-43 proteinopathy according to [5], wherein the virus vector is a lentivirus vector or an adeno-associated virus vector.
[7] The prophylactic or therapeutic composition for TDP-43 proteinopathy according to any of [1] to [4], wherein the RNA comprises at least one or more modified nucleotides.
[8] The prophylactic or therapeutic composition for TDP-43 proteinopathy according to any of [1] to [7], wherein the one or more nucleic acids are encapsulated in nanoparticles.
[9] The prophylactic or therapeutic composition for TDP-43 proteinopathy according to any of [1] to [8], wherein the TDP-43 proteinopathy is SOD1-unrelated amyotrophic lateral sclerosis and frontotemporal lobar degeneration with ubiquitin inclusions.

Advantageous Effects of Invention

The present invention provides a prophylactic or therapeutic composition for TDP-43 proteinopathy based on a suppression of the expression of TDP-43 by microRNA.

BRIEF DESCRIPTION OF DRAWINGS

In the following drawings, the expression level of microRNAs represents a result of TaqMan MicroRNA assay (manufactures by Applied Biosystems, Inc.) and the expression level of proteins represents a result of Western blotting analysis. In the drawings, an asterisk (*) represents p value<0.05 and a double asterisk represents p value<0.01 as a result of significance test.

FIG. 1A shows the result of prediction of the target sequences of microRNAs in the 3'-UTR sequence of the human TDP-43 gene by the use of TargetScan. A short bar represents the position of the target sequence of microRNA that was predicted. Two boxed bars represent the positions of the target sequences of miR-33a/b that were predicted.

FIG. 4A shows a schematic view of the procedure for generating a human iPSC line (TDP-43 KO iPSC), in which TDP-43 has been knocked out.

FIG. 7B shows the result of analyzing the products of genomic PCR carried out for 5 neomycin-resistant clones (Clones 8, 9, 14, 15, and 18) using 3 primer sets (A-C). The primer set B yields a 3,398-bp PCR product from the clone in which the neomycin selection cassette has been inserted in the miR-33a gene, and a 1,747 bp-bp PCR product from the clone in which the neomycin selection cassette has not been inserted. FIG. 7B shows the result of genomic PCR carried out for the clones 15 and 18 using P-a5/P-a6 primer set. Prior to the PCR, both clones were allowed to express Cre recombinase. The clone in which the cassette has been removed yields a 230-bp PCR product, whereas the clone keeping the cassette yields a 1,740-bp PCR product.

DESCRIPTION OF EMBODIMENTS

Figure 1B:
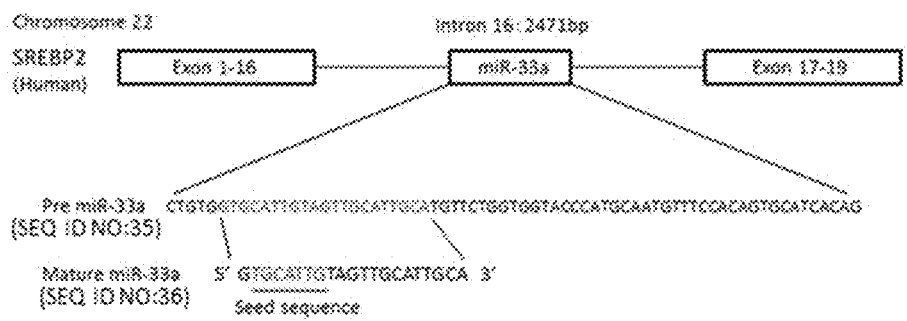
FIG. 1B shows a schematic view of the relationship among miR-33a gene, pre-miR-33a, and mature miR-33a (i.e., guideRNA). The miR-33a gene is encoded in the intron 16 of SREBP-2 gene is located in human chromosome 22. The mature miR-33a is generated from the pre-miR-33a and the pre-miR-33a is generated from the miR-33a gene.

Hereinafter, the preferred embodiments of the present invention will be described in detail.

The term "NR_", "NM_", or "NP_" used herein and numbers following the term refer to ID of the nucleotide sequence of a non-coding RNA gene (NR_XXXXXX), the nucleotide sequence of a transcript (NM_XXXXXX), or the amino acid sequence (NP_XXXXXX) recorded as a reference sequence in NCBI (National Center for Biotechnology Information) database. Only one ID is given as an example for a plurality of reference sequences recorded.

The first aspect of the present invention provides a composition for the prevention or treatment of TDP-43 proteinopathy, including one or more nucleic acids selected from a microRNA targeting TDP-43 gene, a precursor thereof, and an isolated nucleic acid encoding the microRNA or the precursor.

[MicroRNA and Precursor Thereof]

The microRNA, one type of non-coding RNA, is an endogenous gene expression regulator that is expressed in site- and time-specific manners to suppress the expression of a particular gene (=target gene) at the translation stage.

In the process of its biosynthesis, the microRNA gene is transcribed from the genome as a primary microRNA (abbreviated to pri-miRNA), which is then cleaved to generate a precursor miRNA (abbreviated to pre-miRNA) composed of a region of approximately 60 to 100 nucleotides. The pre-miRNA is a hairpin RNA having a hairpin-shaped structure composed of imperfectly paired stem and loop moieties. The pre-miRNA is transported to the cytoplasm where the loop moiety is cleaved by Dicer (RNase III) to generate a double-stranded miRNA. This duplex is further processed into a double-stranded mature miRNA of approximately 18 to 26 bp. Then, the miRNA is incorporated in a double-stranded or single-stranded state into RNA-induced silencing complex (abbreviated to RISC) so that a miRNA-RISC complex including one strand of the mature miRNA is finally formed. The single-stranded mature miRNA that has formed the complex with RISC is called guide strand, and the other single-stranded mature miRNA (which has not formed the complex with RISC) is called passenger strand (Ha M., and Kim N V., Nat. Rev. Mol. Cell Biol., 15:509-524, 2014).

The miRNA-RISC complex performs the cleavage or translational inhibition of target mRNA through base pair formation between the included miRNA (guide strand) and the 3'UTR region of the target mRNA. A sequence in the mRNA necessary for this reaction is called target sequence of the miRNA. In many cases, bases at positions 2 to 8 counted from the 5' end of the mature miRNA are important for the recognition of the target RNA, and this nucleotide sequence is called seed sequence. However, the seed sequence and the target sequence do not have to be completely complementary. In general, the miRNA-RISC complex is considered to recognize the target mRNA through base pair formation including mismatch (Wilson R. C., et al, Annu. Rev. Biophys., 42:217-239, 2013).

A pre-miRNA directly transferred as an RNA molecule to a cell is cleaved by Dicer in the cell to generate a double-stranded miRNA, finally resulting in a single-stranded mature miRNA. When the pre-miRNA is expressed in a cell using an expression vector, a pre-miRNA transcript is also cleaved by Dicer to generate a double-stranded miRNA, finally resulting in a single-stranded mature miRNA.

Accordingly, all of the pre-miRNA, the double-stranded miRNA, and the double-stranded mature miRNA are precursors of the microRNA. The suppressive effect on the expression of the target gene can be obtained by the direct transfer of any of these precursors as an RNA molecule to a cell or by the expression of any of these precursors in a cell using an expression vector.

The Dicer recognizes, as a substrate, a hairpin structure formed by RNA having a length of approximately 60 to 100 nucleotides and cleaves a site some distance from the 5' or 3' end (Macrae I. J., et al, Science, 311:195-198, 2006; Park J. E., et al, Nature, 475:201-205, 2011). The cleavage site by the Dicer is not stringent. In general, a plurality of double-stranded RNAs differing in length are generated from one type of pre-miRNA (Starega-Roslan J., et al, Nucleic Acid Res., 39:257-268, 2011). Hairpin RNAs that may serve as a substrate of Dicer have diverse structures. A large number of pre-miRNAs differing in the length of the stem moiety, the number of gaps (unpaired sites) in the stem and the number of nucleotides constituting the gaps, and the number of nucleotides constituting the loop (Kozomara A., et al, Nucleic Acid Res., 39:D152-D157, 2011; Kozlowski P., et al, Current Perspectives in microRNAs (miRNA), Springer, Houten, pp. 1-16, 2008). Hence, it is known that a sequence known as pre-miRNA is processed into a double-stranded miRNA by Dicer even if a mutation such as base substitution, deletion, or insertion is introduced thereto without destroying the hairpin structure.

The "microRNA" used herein refers to the "guide strand". Accordingly, for example, the "human miR-33" used herein refers to the guide strand of miR-33 represented by SEQ ID NO: 1 (specifically, the guide strand of miR-33a represented by SEQ ID NO: 2 and the guide strand of miR-33b represented by SEQ ID NO: 3), unless otherwise specified.

The "pre-miRNA" used herein encompasses all of pre-miRNA variants that can maintain the sequence of the guide strand and maintain the hairpin structure. This is because these variants can finally generate the guide strand by cleavage by Dicer (i.e., these variants function as the pre-miRNA).

pre-miRNAs that have the same seed sequence and generate single-stranded mature miRNAs with high homology are superordinately conceptualized as a family. For example, in humans, miR-33a (SEQ ID NO: 2) and miR-33b (SEQ ID NO: 3) derived from the seed sequence "UGCAUUG" have been identified, and these pre-miRNAs are called human miR-33 family. As used herein, miR-33a and miR-33b are also collectively referred to as "(human) miR-33".

[MicroRNA Targeting TDP-43 and Precursor Thereof]

The present inventors have revealed that human miR-33 is a microRNA that suppresses the expression of the TDP-43 gene by using a nucleotide sequence from positions 2108 to 2114 (CAAUGCA) in the 3'-UTR sequence (nucleotide sequence from positions 1379 to 4216 of NM_007375) as a target sequence. The present inventors have further found that the activity of targeting the TDP-43 gene is not impaired even if a nucleotide sequence other than the seed sequence (=nucleotide sequence from positions 2 to 8 counted from the 5' end) in the human miR-33 is partially substituted.

Accordingly, all of miR-33a, miR-33b, and variant miR-33a and miR-33b derived therefrom by the partial mutation of a nucleotide sequence other than the seed sequence are included in the microRNA targeting TDP-43.

Precursor of miR-33a

The nucleotide sequence of the guide strand of miR-33a (microRNA 33a, Official Symbol: MIR33A) is represented by SEQ ID NO: 2, and the nucleotide sequence of its pre-miRNA is represented by, for example, NR_029507 (SEQ ID NO: 10). The Pre-miR-33a has been found to form a secondary structure represented by the following chemical formula 1 in cells:

[Formula 1]

(1)

SEQ ID NO: 10

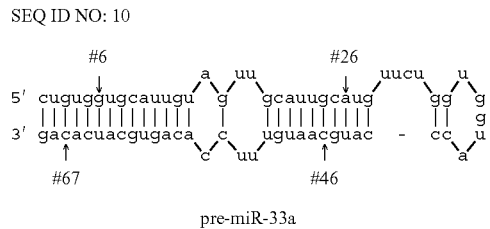

pre-miR-33a

In the above formula, "#" represents the first and the last ribonucleotides in the sequence of guide strand (consisting of the ribonucleotides from the 6th to the 26th) and the sequence of passenger strand (consisting of the ribonucleotides from the 46th to the 67th), respectively.

In the chemical formula 1, nucleotides at positions 6 to 26 counted from the 5' end are a region serving as the guide strand, and nucleotides at positions 46 to 67 are a region serving as the passenger strand. Accordingly, an RNA represented by the chemical formula 1 in which a sequence other than the nucleotides at positions 6 to 26 has been varied (specifically, by base substitution, deletion, and/or insertion) without destroying the stem structure of approximately 28 bp (which consists of the nucleotides at positions 1 to 28 and the nucleotides at positions 42 to 69) and the subsequent loop structure is also included in the pre-miR-33a. The pre-miR-33a represented by the chemical formula 1 has two gaps in the stem moiety, and these gaps may be canceled.

The pre-miR-33a represented by the chemical formula 1 is cleaved, at or near the boundary between the stem moiety and the loop moiety, by Dicer to generate a double-stranded RNA (double-stranded miR-33a), which then becomes a double-stranded RNA in which the nucleotides at positions 6 to 26 (guide strand) and the nucleotides at positions 46 to 67 (passenger strand) are incompletely paired (double-stranded mature miR-33a).

Accordingly, all of the pre-miR-33a (the RNA represented by the chemical formula 1 or a variant thereof) and the double-stranded miR-33a and the double-stranded mature miR-33a derived therefrom are included in the precursor of miR-33a.

Precursor of miR-33b

The nucleotide sequence of the guide strand of miR-33b (microRNA 33b, Official Symbol: MIR33B) is represented by SEQ ID NO: 3, and the nucleotide sequence of its pre-miRNA is represented by, for example, NR_030361 (SEQ ID NO: 11). The Pre-miR-33b has been found to form a secondary structure represented by the following chemical formula 1 in cells:

[Formula 2]

(2)

SEQ ID NO: 11

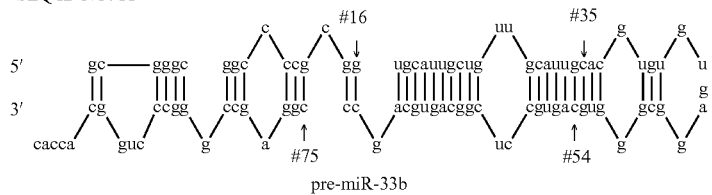

pre-miR-33b

In the above formula, "#" represents the first and the last ribonucleotides in the sequence of guide strand (consisting of the ribonucleotides from the 16th to the 35th) and the sequence of passenger strand (consisting of the ribonucleotides from the 54th to the 75th), respectively.

In the chemical formula 2, nucleotides at positions 16 to 35 counted from the 5' end are a region serving as the guide strand, and nucleotides at positions 54 to 75 are a region serving as the passenger strand. Accordingly, an RNA represented by the chemical formula 2 in which a sequence other than the nucleotides at positions 16 to 35 has been varied (specifically, by base substitution, deletion, and/or insertion) without destroying the stem structure of approximately 37 bp (which consists of the nucleotides at positions 1 to 37 and the nucleotides at positions 51 to 91) and the subsequent loop structure is also included in the pre-miR-33b. The pre-miR-33b represented by the chemical formula 2 has six gaps in the stem moiety, and these gaps may be canceled.

The pre-miR-33b represented by the chemical formula 2 is cleaved, at or near the boundary between the stem moiety and the loop moiety, by Dicer to generate a double-stranded RNA (double-stranded miR-33b), which then becomes a double-stranded RNA in which the nucleotides at positions 16 to 35 (guide strand) and the nucleotides at positions 54 to 75 (passenger strand) are incompletely paired (double-stranded mature miR-33b).

Accordingly, all of the pre-miR-33b (the RNA represented by the chemical formula 2 or a variant thereof), and the double-stranded miR-33b and the double-stranded mature miR-33b derived therefrom are included in the precursor of miR-33a.

Human miR-33 Variant and Precursor Thereof

The human miR-33 variant that can be used in the present invention is a variant that maintains the suppressive activity against the expression of the TDP-43 gene. Examples of such a variant include a variant having a mutation in a nucleotide sequence other than the seed sequence. The mutation can be any of base substitution, deletion, and insertion and is preferably a mutation of 5 or less bases. The mutation is more preferably base substitution, deletion, or insertion of 4 or less bases, 3 or less bases, 2 or less bases, or 1 base. Also, the mutation may be base substitution, deletion, or insertion of 5, 4, 3, or 2 consecutive bases.

The mutation site is most preferably a base other than bases at positions 2 to 8 counted from the 5' end (i.e., a base at position 1 and/or base(s) at or subsequent to position 9) in the nucleotide sequence of SEQ ID NO: 1, still further preferably a site except for bases at positions 12 to 16 (i.e. a base at position 1, base(s) at positions 9 to 11, and/or base(s) at or subsequent to position 17). This is because it has been confirmed that the substitution of the base(s) at positions 9 to 11 and/or the base(s) at or subsequent to position 17 dose not impair the activity of suppressing the expression of the TDP-43 gene by binding to 3'UTR thereof.

Examples of the human miR-33 variant according to the present invention include an RNA having a nucleotide sequence represented by any of SEQ ID NOs: 4 to 6. The variant has TDP-43 expression suppressive activity substantially equivalent to that of miR-33a and miR-33b and can be preferably used in the present invention.

The precursor of the human miR-33 variant according to the present invention is the precursor of miR-33a and/or the precursor of miR-33b containing any of the mutations mentioned above in the sequence of the guide strand.

Modification of Nucleotide/RNA

The microRNA according to the present invention or the precursor thereof can preferably contain a modified nucleotide (including a nucleotide analog) for the purpose of improving stability. Examples of such a modified nucleotide include a ribonucleotide with a modified sugar, a ribonucleotide with a modified backbone, and a ribonucleotide with a modified base.

Examples of the ribonucleotide with a modified sugar that can be preferably used in the present invention include a ribonucleotide in which the 2' OH group of the sugar is substituted by a group selected from H, OR, R, SH, SR, $NH_2$, NHR, $NR_2$, CN, and halogen. The R is a C1-C6 group, preferably a C1-C6 alkyl group, alkoxy group, alkenyl group, or alkynyl group, particularly preferably a methyl group, an ethyl group, a methoxyethyl group, an amino group, an aminopropyl group, or an isopropyl group. The halogen is preferably F, Cl, Br, or I, particularly preferably F.

Among them, a ribonucleotide modified with 2'-fluoro, 2'-O-methyl, or 2'-O-methoxyethyl can be particularly preferably used.

The microRNA according to the present invention or the precursor thereof may contain phosphorothioate so that a phosphorothioate bond is formed between the sugar and the phosphate. The DNA or RNA phosphorothioation can confer high nuclease resistance without influencing the base pair formation and as such, can be particularly preferably used in the present invention.

The microRNA according to the present invention or the precursor thereof may contain a ribonucleotide containing a non-naturally derived base, for example, uridine or cytidine modified at position 5 (e.g., 5-(2-amino)propyluridine and 5-bromouridine), adenosine or guanosine modified at position 8 (e.g., 8-bromo-guanosine), deazanucleotide (e.g., 7-deazaadenosine), and O- and N-alkylated nucleotides (e.g., N6-methyladenosine).

A nucleotide analog such as 2',4'-BNA (bridge nucleic acid) or LNA (locked nucleic acid) in which the 2' oxygen atom and the 4' carbon atom of the sugar are bridged via a methylene bond (Koshkin et al., J. American Chemical Society, 120: 13252-13253, 1998), ENA (2'-O,4'-C-ethylene-bridged nucleic acids) (WO2000/047599), or 4'-thionucleotide in which the oxygen atom of the furanose ring is substituted by a sulfur atom (Dande, P., et al, J. Med. Chem., 49:1624-1634, 2006; and WO2004/18494) can also be preferably used in the present invention.

All of these modified nucleotides are techniques known in the art and are routinely used as methods for improving the in vivo stability of oligonucleic acids (see Summerton and Weller, Antisense Nuc. Acid Drug Dev., 7: 187-195 (1997); and Hyrup et al., Bioorgan. Med. Chem., 4: 5-23 (1996)). In the present invention, a portion or the whole of the microRNA or the precursor thereof may be substituted by one or two or more modified nucleotides selected from the modified nucleotides mentioned above.

The microRNA according to the present invention or the precursor may be conjugated, at its terminal (5'-terminal and/or 3'-terminal) nucleotide, with a peptide, an aptamer, a hydrophobic molecule, or the like for the purpose of tissue-specific delivery or improvement in cell membrane permeability. Preferred examples of the hydrophobic molecule for this purpose include cholesterol, vitamin E (α-tocopherol), and palmitoyl (WO2005/115481; and Uno Y., et al., Human Gene Therapy, 22: 711-719, 2011).

The modifications described above may be used in combination. For example, the phosphorothioated RNA may be conjugated with the peptide, the aptamer, the hydrophobic molecule, or the like mentioned above. Alternatively, different types of the modified nucleotides may be contained at an end and a site other than the end.

According to a preferred embodiment, examples of the microRNA precursor according to the present invention include a double-stranded RNA including a single-stranded RNA (SEQ ID NO: 8) having a phosphorothioated miR-33 sequence, and a single-stranded RNA (SEQ ID NO: 9) which has a sequence complementary to the single-stranded RNA and has cholesterol added at one end (chemical formula 3). This precursor has the advantages that its double-stranded RNA form can penetrate the cell membrane, the RNA strand having the miR-33 sequence is also highly stable in a miRNA-RISC complex, and the precursor permits easy introduction to patients and has highly sustained effects.

[Formula 3]

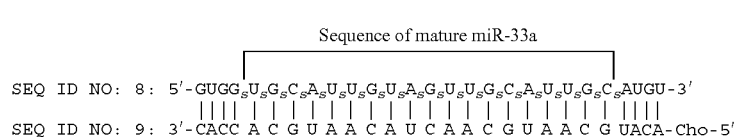

(3)

(In the formula, "Cho" represents cholesterol and "s" represents a phosphorothioate bond)

[Isolated Nucleic Acid Encoding MicroRNA Targeting TDP-43 or Precursor Thereof]

The "isolated nucleic acid" according to the present invention refers to a "nucleic acid separated from a nucleic acid sequence directly adjacent thereto in the genome of an organic from which the nucleic acid is derived". Accordingly, miR-33a encoded in the genome is not an isolated nucleic acid, whereas all of pri-miR-33 transcribed from the genome and subsequent processing products (pre-miR-33a, double-stranded, double-stranded mature, and single-stranded mature terms) are isolated nucleic acids. Also, an artificially synthesized nucleic acid is an isolated nucleic acid, and a DNA fragment amplified by use of PCR is also an isolated nucleic acid.

In the composition according to the present invention, these isolated nucleic acids may each be present independently as a nucleic acid molecule or may be connected to a sequence different from its adjacent sequence in the genome. Accordingly, the artificially synthesized nucleic acid or the DNA fragment amplified by PCR in a state integrated in a plasmid or an expression vector also corresponds to the isolated nucleic acid.

In the present invention, the isolated nucleic acid encoding the microRNA targeting TDP-43 or the precursor thereof is preferably a nucleic acid functionally encoded by an expression vector. In the present invention, the phrase "functionally encoded by an expression vector" means "encoded in the vector in a form that is expressed from the vector" and specifically refers to the state where the nucleic acid encoding the RNA is integrated in the vector in a form functionally joined to a promoter and a control sequence necessary for the termination of transcription (terminator sequence, etc.). The nucleic acid functionally encoded by an expression vector may be any of a DNA and an RNA.

Examples of the promoter that can be preferably used include: RNA polymerase II promoters such as SV (simian virus) 40 promoter, CMV (cytomegalovirus) promoter, β-actin promoter, EF (elongation factor) 1α promoter, and CAG promoter; and RNA polymerase III promoters such as U6 and H1 promoters.

The nucleic acid encoding the microRNA targeting TDP-43, etc., may be any of a DNA and an RNA.

The expression vector that can be preferably used for the purpose may be any of a virus vector and a non-viral vector. A virus vector is preferred.

Examples of the virus vector that can be used in the present invention include, but are not limited to, recombinant adenovirus and retrovirus and more specifically include detoxified lentivirus, adeno-associated virus, herpesvirus, vaccinia virus, and poliovirus. Among them, lentivirus and adeno-associated virus are preferred, and adeno-associated virus is most preferred.

The adeno-associated virus has yielded results in clinical trials on the gene therapy of Parkinson's disease, Alzheimer's disease, etc. In addition, the adeno-associated virus has been reported to express a gene or a microRNA in a neural-specific manner in mouse models of various neurodegenerative diseases and thereby exert therapeutic effects (see Japanese Patent No. 4279141). Thus, the adeno-associated virus can be particularly preferably used in the present invention. For example, it has been reported that: a composition including adeno-associated virus encoding miR-196a under the control of CMV promoter was injected to the skeletal muscle of mouse models of spinal and bulbar muscular atrophy so that the vector arrived at cells of spinal cord motor neurons through retrograde axonal transport to suppress the expression of the target gene, producing therapeutic effects (Miyazaki Y., et al., Nat. Medicine, 18: 1136-1144, 2012); and a composition including adeno-associated virus encoding ADAR2 gene under the control of a neural-specific promoter (synapsis gene promoter) was intravenously injected to ALS mouse models so that the gene was specifically expressed in neurons, producing therapeutic effects (Yamashita T., et al., EMBO Mol. Med., 5: 1710-1719, 2013). These techniques may be applied to the present invention.

The virus vector mentioned above can be prepared by a method known in the art, also including alteration of the promoter.

Examples of the non-viral vector include, but are not limited to, pSilencer H1-puro (Applied Biosystems, Inc.) and BLOCK-iTTMPol II miR RNAi Expression Vector (Invitrogen Corp.). These non-viral vectors are commercially available.

[Composition for Prevention or Treatment of TDP-43 Proteinopathy]

The composition for the prevention or treatment of TDP-43 proteinopathy according to the present invention includes, as an active ingredient, one or more nucleic acids selected from the microRNA targeting TDP-43, the precursor, and the isolated nucleic acid encoding the microRNA or the precursor. The composition according to the present invention can contain a pharmaceutically acceptable carrier, diluent, excipient, adjuvant, and the like, in addition to the active ingredient and can be produced by an ordinary method pharmaceutically used.

According to a preferred embodiment, examples of the composition according to the present invention include a liquid composition. The liquid composition may be produced by dissolving or suspending the active ingredient in a pharmaceutically acceptable liquid carrier. A liquid carrier known in the art, for example, water, physiological saline, an injectable aqueous solution, or a Ringer's solution can be used as the liquid carrier. The liquid carrier may further contain a pharmaceutically acceptable salt. When the composition according to the present invention contains the isolated nucleic acid, a carrier for nucleic acid drugs may be further added thereto as the liquid carrier. Examples of such a carrier include cationic lipid and atelocollagen (Japanese Patent No. 5145557). When the composition according to the present invention contains the nucleic acid encoded by the virus vector, one or more dihydric alcohols or polyhydric alcohols and a nonionic surfactant (e.g., sorbitan ester and TWEEN compounds) may be further added thereto as the excipient (see WO00/32233).

The liquid composition according to the present invention may be produced by encapsulating the active ingredient in nanoparticles for drug delivery and then suspending the nanoparticles in the pharmaceutically acceptable liquid carrier. The nanoparticles for drug delivery are a particle dispersion or solid particles with a particle size of 10 to 1000 nm prepared from diverse materials such as lipids, proteins, polysaccharides, and synthetic polymers. Examples thereof include liposomes, micelles, metal nanoparticles, and polymer nanoparticles. Specific examples of the liposomes include, but are not limited to, liposomes composed mainly of N-[2,3-(dioleyloxy)propyl]-N,N,N-trimethylammonium chloride (DOTMA) or dioleoylphosphatidylethanolamine (DOPE). Also, the nanoparticles may be surface-modified with various substances for the purpose of improving biocompatibility and delivery characteristics.

These nanoparticles for drug delivery may be produced according to a method well known to those skilled in the art.

According to a preferred embodiment, examples of the liquid composition according to the present invention include a dispersion of nanoparticles made of poly-lactide-co-glycolide (PLGA) (PLGA nanoparticles) with the active ingredient encapsulated therein. The average particle size of the PLGA nanoparticles is 50 to 200 nm, more preferably 60 to 150 nm, most preferably 70 to 100 nm, in terms of a value determined by a dynamic light scattering method. The particle surface may be modified with chitosan. Also, the dispersion may contain a dispersion stabilizer (e.g., polyvinyl alcohol) and a pH adjuster (e.g., citric acid hydrate).

The production of the PLGA nanoparticles and the encapsulation of the active ingredient according to the present invention in the particles may be carried out according to methods described in, for example, Japanese Patent No. 4340744. Since the PLGA nanoparticles are excellent in biocompatibility, biodegradability, and sustained release, the aforementioned dispersion of the PLGA nanoparticles with the active ingredient according to the present invention encapsulated therein can also be used as an inhalant, an intramuscular injection, a stent, or the like (see Tsukada Y., et al., New Developments in Polylactic Acid Research, published by Nova Science Publishers, Chapter 6, pp. 153-182, 2015; and Yusuke Tsukada et al., Development and practical use of novel DDS products opened up by PLGA nanoparticles, Medicine and Drug Journal, Vol. 50, p. 73-80, 2014).

[Administration Method]

The composition for the prevention or treatment of TDP-43 proteinopathy according to the present invention can be administered to a patient by use of a method known in the art. For example, the liquid composition may be systemically administered through intravenous injection or transfusion or may be locally administered to the cerebral ventricle or the spinal canal using stereotactic injection, a needle, a catheter, an osmotic pressure pump, an infusion pump, a drug-eluting stent, or the like. When the composition according to the present invention contains the active ingredient in a state encoded by a virus vector, this composition may be administered to the muscle (preferably, the skeletal muscle) through stereotactic injection.

A method for drug delivery by the injection of a needle or a catheter to the cerebral ventricle or the spinal cord is known in the art (Stein et al., J. Virol, 73:3424-3479, 1999; Davidson et al., PNAS, 97:3428-3432, 2000; Alisky and Davidson, Hum. Gene Ther., 11:2315-2329, 2000 etc). Drug delivery to the brain using an osmotic pressure pump or an infusion pump is well known as convection-enhanced delivery (CED) (U.S. Pat. No. 6,309,634). For example, U.S. Pat. Nos. 5,735,814, 6,042,579, and 5,814,014 disclose injection systems into the brain using an implantable pump and catheter. Any of these methods may be used. A large number of apparatuses for drug delivery to the brain and the spinal cord are also commercially available (e.g. SynchroMed®, manufactured by EL Infusion System). Any of these apparatuses may be used.

The dose and the dosing frequency can be adjusted according to various factors such as the presence or absence of a TDP-43 gene mutation in the subject, the severity of symptoms, age, and body weight. Alternatively, the dose and the dosing frequency may be determined by measuring TDP-43 concentration in the cerebrospinal fluid of the subject. The dose and the dosing frequency at which the TDP-43 concentration in the cerebrospinal fluid of the subject is decreased within a range that does not fall below the corresponding concentration of healthy individuals (normal range) may be judged as being effective.

In the present invention, the "healthy individual" means an individual having no TDP-43 proteinopathy.

The composition for the prevention or treatment of TDP-43 proteinopathy according to the present invention may be used in combination with an additional drug. When the target disease is, for example, ALS, examples of the drug for combined use therewith can include riluzole (trade name: Rilutek® (Sanofi K. K.)), which is an existing therapeutic drug for ALS, a 1,3-diphenylurea derivative or a multikinase inhibitor described in WO2012/029994, a HMG-CoA reductase inhibitor described in WO2011/074690, and anacardic acid (Egawa, N et al., Sci Transl Med. 4 (145): 145ra104.doi: 10.1126). These drugs can be used, for example, at a dose and through an administration route usually used in the treatment of ALS.

[Target Disease]

The composition according to the present invention can be preferably administered as a prophylactic or therapeutic drug to a TDP-43 proteinopathy patient and a patient suspected of having the disease. The TDP-43 proteinopathy is neurodegenerative diseases with the structural abnormality and intracellular localization abnormality of the TDP-43 protein. Typical examples of this disease include a great majority of sporadic ALS cases, many SOD1-unrelated familial ALS cases, and a great majority of sporadic and familial FTLD-U cases.

Alternatively, the composition according to the present invention may be used as a prophylactic drug for TDP-43 proteinopathy for a patient having a pathologically high TDP-43 concentration in the cerebrospinal fluid.

[Neuron and Motor Neuron]

In the present invention, the neuron (also abbreviated to N) is defined as a cell that expresses one or more neuronal marker genes such as β-III tubulin, NCAM, and MAP2 and has neurites. In the present invention, the motor neuron (also abbreviated to MN) is defined as a neuron that expresses one or more motor neuron marker genes such as HB9 and ChAT (choline acetyltransferase).

In recent years, there have frequently occurred the cases where drugs effective for animal (mainly, mouse) models of various diseases do not exhibit efficacy in clinical trials. Thus, the difference between human cells and mouse cells has been reviewed. Particularly, neurons cannot be isolated from humans by a low invasive method. Therefore, neurons and motor neurons obtained by the differentiation induction of iPSC (abbreviated herein to iPSC-N and iPSC-MN) have been greatly expected as a drug evaluation system. Attempts to test drug toxicity or effectiveness using cells differentiated from human iPSC have already made many achievements in the fields of heart diseases and hepatic diseases (Guo L., et al., Toxicol. Sci., 123: 281-289, 2011; Medine C. N., et al., Stem Cells Transl. Med., 2: 505-509, 2013; and Scott C. W., et al., Toxicol. Lett., 219: 49-58, 2013). Drug toxicity tests using iPSC-derived differentiated cells are being regarded as preclinical trials (Inoue H., et al., EMBO, 33:409-417, 2014). Also in the field of neurological diseases, the phase II clinical trial of ALS in the USA is scheduled for an existing drug (antiepileptic drug retigabine) confirmed to be effective in neurons differentiated from iPSC (ClinicalTrials.gov Identifier: NCT02450552, clinicaltrials.gov/ct2/show/NCT02450552).

Human miR-33 is a TDP-43 expression suppressor carried by human iPSC-derived neurons and therefore, probably serves as an effective agent suppressing TDP-43 expression for humans.

According to the second aspect, the present invention further provides a method for preventing or treating TDP-43 proteinopathy by administering one or more nucleic acids selected from a microRNA targeting the TDP-43 gene, a precursor thereof, and an isolated nucleic acid encoding the microRNA or the precursor to a recipient. The microRNA, the precursor thereof, the administration method, and the target disease, etc., are as mentioned above.

miR-33a is a microRNA encoded in intron 16 of the SREBP-2 (sterol regulatory element-binding transcriptional factor 2, Official Symbol: SREBF2, NM_004599) gene that resides on human chromosome 22. miR-33b is a microRNA encoded in intron 17 of the SREBP-1 (sterol regulatory element-binding protein 1, Official Symbol: SREBF1, NM_001005291) gene that resides on human chromosome 17.

SREBP-1 and SREBP-2 are transcriptional factors that play a central role in fatty acid metabolism and cholesterol metabolism, respectively (Brawn M. S., and Goldstein J. L., Cell, 89: 331-340, 1997). Human miR-33 and mouse miR-33 target ATP-binding cassette transporter A1 (ABCA1) responsible for the retrograde transport of cholesterol. The suppressed expression of miR-33 has been found to ameliorate arteriosclerosis (Horie T. et al., Nat. Commun., 4: 2883, 2013). Therefore, anti-miR of human miR-33 is very expected as a therapeutic drug for cholesterol-related diseases (e.g., National Publication of International Patent Application No. 2012-522509).

As mentioned above, human miR-33 has received a great deal of attention in relation to diseases of fatty acid and cholesterol metabolisms and has received no attention so far in the fields of the nervous system and neurological diseases. Results of previous genome-wide association studies conducted for ALS patients are maintained in a public database (ALSGebe-GWAS, www.alsgene.org/). However, there has been no report about a polymorphism correlating with the disease in the miR-33a gene sequence and in a miR-33a target sequence found in the TDP-43 gene.

Accordingly, use (method) of human miR-33 itself, not anti-miR, as a therapeutic drug and use (method) of the human miR-33 as a therapeutic drug for neurodegenerative diseases have been found for the first time by the present invention.

EXAMPLES

The present invention is described below in more detail by way of Examples, but the scope of the present invention is not limited to the Examples. The main experimental procedures used in Examples below will first be described, and the sequences of the oligonucleotides used are shown in Table 1.

TABLE 1

| Name of oligonucleotide | Nucleotide sequence | SEQ ID NO |
|---|---|---|
| Generation of Knockout iPSC (Examples 3, 4) | | |
| miR-33a KO gRNA-1a | GCTGCCCGCCAGGAGGTATGCGG | SEQ ID NO: 13 |
| miR-33a KO gRNA-2a | TGTAGTTGCATTGCATGTTCTGG | SEQ ID NO: 14 |
| TDP-43 KO TALEN-L | TTTTCTCTTTAGGAAAAG | SEQ ID NO: 15 |
| TDP-43 KO TALEN-R | TATATTCGGGTAACCGAA | SEQ ID NO: 16 |
| Knockout clone screening (Examples 3, 4) | | |
| miR-33a KO P-a1 | CCTGTGTCTCTGACTTCCAG | SEQ ID NO: 17 |
| miR-33a KO P-a2 | CCAGAGGCCACTTGTGTAGC | SEQ ID NO: 18 |
| miR-33a KO P-a3 | CTTCTTGACGAGTTCTTCTG | SEQ ID NO: 19 |
| miR-33a KO P-a4 | AGGGTGGCTGCAAGCCTCTC | SEQ ID NO: 20 |
| miR-33a KO P-a5 | CTGTGGCGCAACGCAATTAG | SEQ ID NO: 21 |
| miR-33a KO P-a6 | TTCCTGGGATGGCTGTGAC | SEQ ID NO: 22 |
| TDP-43 KO P-t1 | GGTGTCCCTGTCGGGCTTCC | SEQ ID NO: 23 |
| TDP-43 KO P-t2 | CCAGAGGCCACTTGTGTAGC | SEQ ID NO: 24 |
| TDP-43 KO P-t3 | CCGATTCGCAGCGCATCGCC | SEQ ID NO: 25 |

TABLE 1-continued

| Name of oligonucleotide | Nucleotide sequence | SEQ ID NO |
|---|---|---|
| TDP-43 KO P-t4 | ATTCTCCTGCGTCTGCCTCC | SEQ ID NO: 26 |
| TDP-43 KO P-t5 | CCATCGCGCAACGCAATTAG | SEQ ID NO: 27 |
| TDP-43 KO P-t6 | GGCAGAGAGAAGGATAAGACCAG | SEQ ID NO: 28 |
| qRT-PCR (Examples 3) | | |
| human TDP-43-Fw | TGAATATATTCGGGTAACCGAAG | SEQ ID NO: 29 |
| human TDP-43-Rv | CTGTAACCGTGGAGAGCAGC | SEQ ID NO: 30 |
| RNA immunoprecipitation assay (Examples 3) | | |
| pri miR-33a RIP-Fw | CCACAGTGCATCACAGAGGCC | SEQ ID NO: 31 |
| pri miR-33a RIP-Rv | ATAGGGCCTTCAGTCAGGGC | SEQ ID NO: 32 |
| pri miR-17 RIP-Fw | TAGCATTATGGTGACAGCTGC | SEQ ID NO: 33 |
| pri miR-17 RIP-Rv | AGCAGGCCCTGCACTTTAAAG | SEQ ID NO: 34 |

[Procedure 1] 3'UTR Luciferase Reporter Assay
<Preparation of Reporter Gene and Preparation of Cell for Assay>

Total RNA extracted from a healthy individual-derived iPSC line (201B7 line) was used as a template in PCR to obtain a DNA fragment containing the full-length 3'UTR of the human wild-type TDP-43 gene. The 3'UTR region was cloned into PNL2.2[NlucP/Hygro] vector (manufactured by Promega Corp.) to prepare a NlucP luciferase gene (="Normal" in FIG. 1D) that was driven by SV40 promoter and had the full-length human wild-type TDP-43 3'UTR as 3'UTR. Hereinafter, the NlucP luciferase gene is also referred to as a "wild-type reporter gene".

Three types of variant reporter genes were further prepared (="Del1", "Del2", and "Del1+2" in FIG. 1D) by deleting 7mer-1A, 7mer-m8, or 7mer-1A and 7mer-m8 regions from the 3'UTR of the wild-type reporter gene using In-Fusion HD cloning kit (manufactured by Clontech Laboratories, Inc.).

A firefly luciferase gene driven by thymidine kinase promoter (pRL-TK vector, manufactured by Promega Corp.) was used as a reporter gene for an internal control.

HEK293T cell lines having inserts of any of the 4 types of reporter genes and the internal control gene in their genomes were prepared by the Tol2 transposon method.
<Preparation of Lentivirus Functionally Encoding miR-33a or miR-33b>

Genomic DNA extracted from 201B7 iPSC was used as a template in PCR to obtain a DNA fragment containing the human pre-miR-33a represented by SEQ ID NO: 10. The pre-miR-33a region was cloned into pHL-H1-ccdB-mEF1a-RiH vector (available as plasmid #60601 from Addgene) to prepare a plasmid encoding pre-miR-33a whose initiation of the transcription was controlled by a H1 promoter and termination of the transcription was caused by poly(T)$_7$ (hereinafter, referred to as a "wild-type miR-33a expression plasmid"). A DNA fragment containing the pre-miR-33a transcription unit (i.e., from the H1 promoter to the poly(T)$_7$) was cleaved out of the wild-type miR-33a expression plasmid and subcloned into Lenti-6PW (manufactured by Life Technologies Corp.) to prepare a lentivirus encoding pre-miR-33a whose initiation of the transcription was controlled by the H1 promoter and termination of the transcription was caused by poly(T)$_7$ (hereinafter, referred to as "H1::miR-33a Lenti").

A lentivirus encoding pre-miR-33b (SEQ ID NO: 11) that was driven by the H1 promoter and transcriptionally terminated by poly(T)$_7$ (hereinafter, referred to as "H1::miR-33b Lenti") was prepared by the same procedures as above.

Lenti-6PW encoding the "pre-mRNA control insert" (SEQ ID NO: 12; amplified by PCR) of pcDNA6.2-GW/EmGFP-miR-neg Control vector (manufactured by Invitrogen Corp.) instead of the pre-mild-33a (hereinafter, referred to as "H1::miR-con Lenti") was prepared as a control.
<Preparation of Plasmid Functionally Encoding miR-33a Variant>

Mutations were introduced to the wild-type miR-33a expression plasmid to prepare plasmids functionally encoding 4 types of miR-33a variants (Mutants 1 to 4) shown in FIG. 2 (hereinafter, these plasmids are referred to as "miR-33a variant expression plasmids").

A plasmid encoding the "pre-miRNA control insert" instead of the pre-miR-33a under the control of the H1 promoter (hereinafter, this plasmid is referred to as a "miR-con expression plasmid") was prepared as a control.
<Luciferase Reporter Assay>

In Example 1, the HEK293T cell line for assay was infected with the H1::miR-33a Lenti or the H1::miR-con Lenti, and 24 hours later, the activity of the NlucP luciferase and the firefly luciferase was measured using Nano-Glo and One-Glo luciferase assay systems (manufactured by Promega Corp.). The NlucP luciferase activity was normalized with the firefly luciferase activity and evaluated as a relative value to that in the control cells (i.e., the cells infected with H1::miR-con Lenti).

In Example 2, the HEK293T cell line for assay was lipofected with each of the miR-33a variant expression plasmids or the miR-con expression plasmid, and 48 hours later, the activity of the NlucP luciferase and the firefly luciferase was measured and evaluated by use of the same procedure as in Example 1.
[Procedure 2] Preparation of miR-33a-Knockout iPSC A guide RNA pair (miR-33a KO gRNA-1a represented by SEQ ID NO: 13 and miR-33a KO gRNA-2a represented by SEQ ID NO: 14) capable of introducing a double-strand break in the neighborhood of the seed sequence of the miR-33a gene was designed using CRISPR Design (crispr.mit.edu/) provided by Massachusetts Institute of Technology without charge, and cloned into expression vectors. Also, a genome region containing the miR-33a gene was amplified by PCR to prepare a construct in which the amplified nucleic acids were located as homologous arms upstream and downstream of a neomycin selection cassette having loxP sequences at both ends (hereinafter, this construct is referred to as "donor plasmid 2").

$1\times10^6$ cells of a human healthy individual-derived iPSC line (201B7) were transfected with 3 μg each of the gRNA-1a and gRNA-2a expression plasmids, 10 μg of the donor plasmid 2, and 5 μg of a Cas9N double nicking plasmid using Nepa21 electroporator (manufactured by Nepa Gene Co., Ltd.) and inoculated onto feeder cells (Cho S. W., et al., Genome Res., 24: 1012-1019, 2014). After culture for 1 day in an ES medium containing 10 μM Y-27632, neomycin-resistant colonies were obtained by screening using neomycin over 3 to 13 days after the transfection. Clones were prepared from the resistance colonies and subjected to genomic PCR using 3 primer sets (A, B, and C). The primer set A (P-a1 and P-a2) and the primer set C (P-a3 and P-a4) yield 1,038-bp and 1,084-bp PCR products, respectively, regardless of the presence or absence of the selection cassette insert, whereas the primer set B (P-a1 and P-a4) yields a 3,398 bp in the presence of the selection cassette insert and a 1,747-bp PCR product in the absence of the insert (FIG. 7B). As a result, 5 clones were obtained as clones that produced a 3,398-bp product with the primer set B (i.e., clones containing the insert of the neomycin selection cassette in their chromosomes).

The 5 clones were each transfected with a Cre recombinase expression plasmid and subjected to genomic PCR using a primer set (P-a5 and P-a6) to select clones free from the selection cassette. Then, the clones were sequenced to confirm that the cassette was removed from the genomic DNAs of the clones and the hall length or a portion of the seed sequence in the miR-33a gene was deleted.

The nucleotide sequences of the primers P-a1 to P-a6 are shown in Table 1 as SEQ ID NOs: 17 to 22.

[Procedure 3] Induction of Differentiation of iPSC into MN

Motor neurons (also abbreviated herein to MN) were differentiation-induced from iPSC by use of SFEBq (quick embryoid body-like aggregate method) method (see Egawa N., et al., Science Translational Medicine, 4: 145ra104, 2012). Specifically, human iPSC was dissociated into single cells. The culture of the cells was started in a 5% DFK medium (5% KSR medium (5% DFK), Dulbecco's modified Eagle's medium/Ham's F12 (manufactured by Sigma-Aldrich Co. LLC), 5% KSR (manufactured by Invitrogen Corp.), minimum essential medium-nonessential amino acids (Invitrogen Corp.), L-glutamine (manufactured by Sigma-Aldrich Co. LLC), and 2-mercaptoethanol (Wako Pure Chemical Industries, Ltd.)) containing 2 μM dorsomorphin and SB431542 using a U-shaped 96-well plate coated with Matrigel (manufactured by BD Biosciences) (the start day of the culture was defined as the start day of differentiation induction (i.e., Day 0)). The cells were reaggregated by culture for 12 days. Then, the cells were cultured in a neurobasal medium containing B27 supplement, 1 μM retinoic acid, and 1 mM smoothened agonist. On Day 22, the aggregates (adherent embryoid bodies) were inoculated to a Matrigel-coated dish and attached thereto. The adherent embryoid bodies were cultured in a neurobasal medium containing 10 ng/ml BDNF, 10 ng/ml GDNF, and 10 ng/ml NT-3. On Day 35 the embryoid bodies were dissociated into single cells or small masses using Accutase (manufactured by Innovative Cell Technologies, Inc.) and inoculated as neurons at the P3 maturation stage at a cell density of 500,000 cells/ml to a Matrigel-coated 24-well dish.

In this method, cells differentiated into MN are obtained on Day 35 or later, and the number of MN is increased by approximately Day 50. This culture system is a heterogeneous cell population including cells differentiated into MN and the other neurons (see Egawa N., et al., Science Translational Medicine, 4: 145ra104, 2012).

[Procedure 4] Preparation of Pure Culture of iPSC-MN iPSC that underwent the induction of differentiation into MN according to the Procedure 3 was infected with lentivirus encoding a GFP gene driven by HB9 promoter (HB9:: GFP lentivirus; see Egawa N., et al., Science Translational Medicine, 4: 145ra104, 2012) so as to be able to identify live cells differentiated into MN on the basis of GFP fluorescence. On Day 50, the cells were dissociated into single cells using Accutase, then applied to FACS Aria II (manufactured by BD Biosciences), and analyzed with FACS Diva software (manufactured by BD Biosciences) to sort GFP-positive cells (i.e., MN) from other cells. Also, dead cells were removed by 7-aminoactinomycin-D (7-AAD, manufactured by BD Biosciences) staining. The obtained GFP-positive live cells were inoculated at a cell density of 20,000 to 30,000 cells/well to Matrigel-coated 96-well plates to prepare a pure culture of iPSC-MN.

[Procedure 5] Measurement of miR-33a and miR-33b Expression Levels

Total RNA was extracted from cells using miRNeasy mini/macro kit (manufactured by Qiagen N.V.). The miR-33a, miR-33b, and U6 RNA levels were measured using hsa-miR-33a detection kit (Assay ID: 000424, Assay Name: hsa-miR-33a), hsa-miR-33b detection kit (Assay ID: 001565, Assay Name: hsa-miR-33b), and U6 snRNA detection kit (Assay ID: 001973, Assay Name: U6 snRNA), respectively, of TaqMan MicroRNA Assays (manufactured by Applied Biosystems, Inc.). The obtained signals were analyzed using StepOne software v2.1 (manufactured by Applied Biosystems, Inc.). The signals of miR-33a and miR-33b were each indicated as a relative value to the signal of U6 snRNA.

[Procedure 6] Measurement of TDP-43 Expression Level

TDP-43 mRNA level: Total RNA was extracted from cells using miRNeasy mini/macro kit (manufactured by Qiagen N.V.) and subjected to qRT-PCR using human TDP-43-Fw (SEQ ID NO: 29) and human TDP-43-Rv (SEQ ID NO: 30). The signal of the obtained PCR product was quantified. The FDP-43 mRNA level was indicated as a relative value to the signal of GAPDH.

TDP-43 protein level: Cells or tissues were disrupted by sonication in a lysis buffer (containing Complete mini protease inhibitor and phosphatase inhibitor (manufactured by F. Hoffmann-La Roche, Ltd.)) containing 1% SDS to obtain cell extracts. The extracts (corresponding to 20 μg of the protein) were subjected to Western blotting using an anti-TDP-43 antibody (manufactured by ProteinTech Group, diluted 1:1000-fold) to measure a TDP-43 protein level. The TDP-43 protein level was indicated as a relative value to the protein level of β-actin.

[Procedure 7] Measurement of Cholesterol Content

Approximately 500,000 cells of iPSC-N were recovered by centrifugation, and the total cholesterol level was measured using Cholesteryl Ester Assay Kit (manufactured by BioVision, Inc.). EnVision Multilabeled Reader (manufactured by PerkinElmer, Inc.) was used in analysis to measure the absorbance at 570 nm.

[Procedure 8] Measurement of Neurite Length

The neurite length of iPSC-MN was measured using IN Cell Analyzer 2000 or 6000 (manufactured by GE Healthcare Japan Corp.). The total length of GFP-positive neurites in the field of view was measured and divided by the number of GFP-positive cells to calculate a neurite length per iPSC-MN. Eight fields of view were analyzed for each experiment, and the mean and standard error thereof were calculated.

The significance test on the results obtained in Examples of the present application was conducted using the two-tailed Student's t-test or the Dunnett's post hoc test. Significance was confirmed at P value<0.05.

[Example 1] Identification of microRNA Targeting Human TDP-43 Gene

In order to identify a microRNA capable of suppressing the expression of human TDP-43 gene, the 3'-UTR sequence (nucleotide sequence from positions 1379 to 4216 of NM 007375, a total of 2838 nt) of the human TDP-43 gene (mRNA) was analyzed using the public microRNA target prediction program TargetScan version v6.2 (www.targetscan.org/). TargetScan is a program by which the already registered target sequences of microRNAs are searched with respect to an analyte mRNA sequence, and a potential target sequence is evaluated in consideration of the conservation rate of the target sequence among the genomes of different species and results of thermodynamic modeling between the RNA molecules. The analysis results are shown in FIG. 1A.

As shown in FIG. 1A, the 3'-UTR sequence of the human TDP-43 gene was predicted to contain sequences that might serve as targets of 40 types of microRNA families. Those sequences were "conserved sites for miRNA families broadly conserved among vertebrates", which mean to be very high potential target sequences, for 34 types of microRNA families and "conserved sites for miRNA families broadly conserved only mammals", which mean to be high potential target sequences, for 6 types of microRNA families.

On the other hand, TargetScan also predicted "poorly conserved sites for miRNA families conserved among mammals or vertebrates" for 58 types of microRNA families (FIG. 1). These microRNAs were judged as having the low probability of targeting the human TDP-43, though sequences highly homologous to the target sequences thereof were found in the 3'-UTR sequence of the human TDP-43 gene.

The present inventors focused attention on the miR-33 family (specifically, miR-33a and miR-33b) predicted as the microRNAs having the low possibility. As mentioned above, the human miR-33 is a microRNA known to contribute to the metabolic control of fatty acid and cholesterol by targeting ABCA1 gene. By the previous research, the present inventors found that ALS-MN having a TDP-43 gene mutation showed no marked change in the expression of a gene group involved in fatty acid metabolism, but showed decrease in the expression of genes involved in the biosynthesis of steroid and sterol (Patent Document 1 and Non Patent Document 7). The present inventors were interested in this prediction result.

Thus, it was studied whether the human miR-33 could target the sequence using 3'UTR luciferase reporter assay (Procedure 1).

FIG. 1B shows the position of miR-33a gene on the genome, the nucleotide sequence of pre-miR-33a, and the sequence of mature miR-33a (guide strand). As mentioned above, miR-33a is encoded in intron 16 of SREBP-2 gene.

Figure 1C:
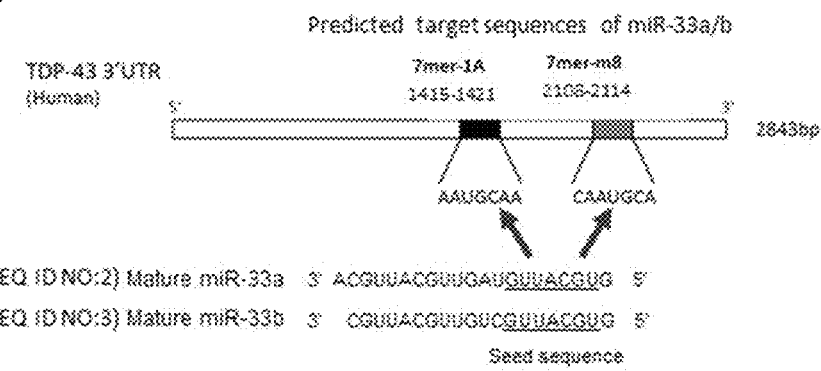
FIG. 1C shows the target sequences of miR-33a and miR-33b (7mer-1A, 7mer-m8) that were predicted in the 3'-UTR sequence of the human TDP-43.

The target sequences of miR-33a and miR-33b predicted by TargetScan are "AAUGCAA" (hereinafter, referred to as "7mer-1A") consisting of nucleotides at positions 1415 to 1421 and "CAAUGCA" (hereinafter, referred to as "7mer-m8") consisting of nucleotides at positions 2108 to 2114 in the 3'-UTR sequence (full length: 2843 nt) of human TDP-43 mRNA (FIG. 1C).

Figure 1D:
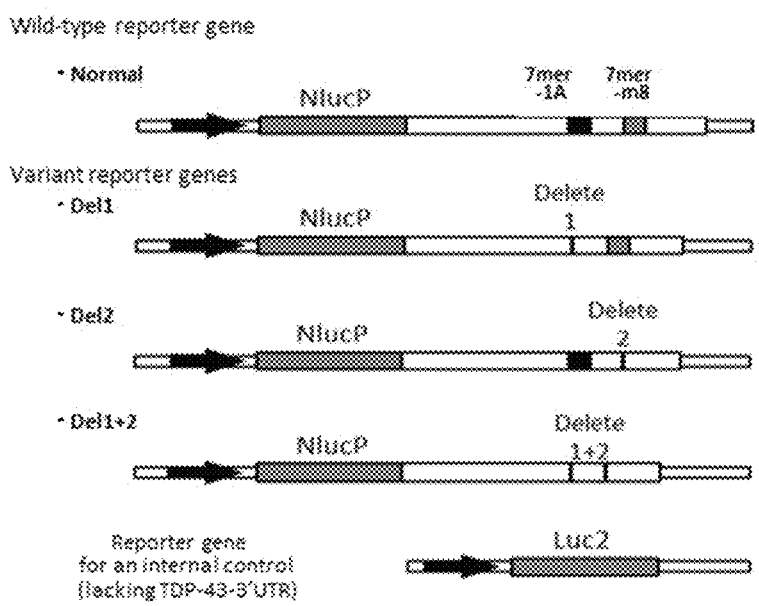
FIG. 1D shows reporter genes (4 types) and an internal control gene used for the 3'UTR luciferase reporter assay.
Figure 1E:
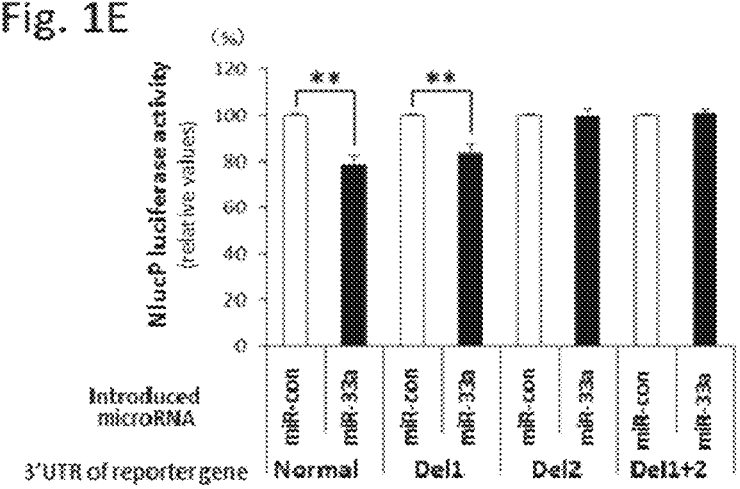
FIGS. 1E and 1F show the results of 3'UTR luciferase reporter assay of the HEK293T cell line at 24 hours after the cell line was infected with either H1::miR-33a Lenti or H1::miR-con Lenti (FIG. 1E), or either H1:: miR-33b Lenti or H1::miR-con Lenti (FIG. 1F) (n=3, mean±standard error). Prior to the infection, any one of the 4 types of reporter genes and the internal control gene shown in FIG. 1D had been introduced into the HEK293T cell line.

A HEK293T cell line harboring any one of the 4 types of reporter genes shown in FIG. 1D and an internal control gene was infected with H1::miR-33a Lenti or H1::miR-con Lenti, followed by luciferase assay (FIG. 1E). The 4 types of reporter genes were a NlucP luciferase gene having the full-length 3'UTR of the human TDP-43 gene as 3'UTR (Normal), a NlucP luciferase gene lacking only 7mer-1A in the 3'UTR (Del1), a NlucP luciferase gene lacking only 7mer-m8 (Del2), and a NlucP luciferase gene lacking only lacking both of 7mer-1A and 7mer-m8 (Del1+2).

As shown in FIG. 1E, the infection of the cells harboring Normal with H1::miR-33a Lenti reduced NlucP luciferase activity to approximately 80% as compared with the infection with H1:miR-con Lenti. This result indicates that miR-33a can suppress the expression of a gene having the 3'UTR of the TDP-43 gene as 3'UTR.

Likewise, the infection of the cells harboring Del1 with H1::miR-33a Lenti also reduced NlucP luciferase activity (approximately 83% with respect to the cells infected with H1::miR-con Lenti). By contrast, the infection with H1::miR-33a Lenti did not reduce NlucP luciferase activity in the cells harboring Del2 or Del1+2. These results indicate that the 7mer-m8 region in the 3'UTR is essential for the suppression of the expression of the reporter gene by miR-33a.

Accordingly, it was demonstrated that miR-33a is a microRNA targeting the TDP-43 gene and the 7mer-8m region in the 3'UTR of the gene is the target sequence of miR-33a.

Figure 1F:
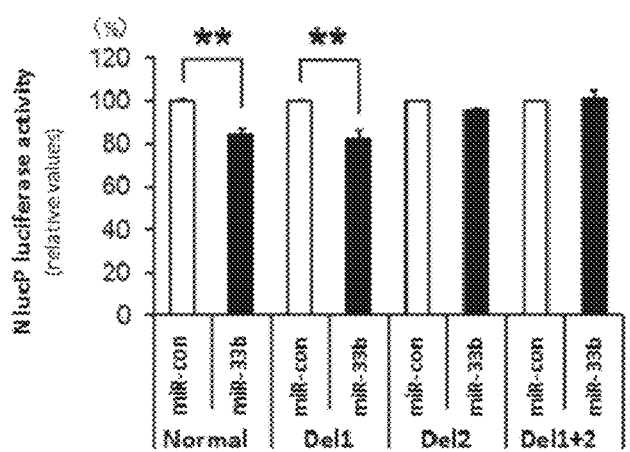

Results of conducting similar analysis on miR-33b are shown in FIG. 1F. The results demonstrated that miR-33b is also a microRNA targeting the TDP-43 gene and the 7mer-8m region in the 3'UTR of the gene is the target sequence of miR-33b.

It was thus concluded that the human miR-33 (miR-33a and miR-33b) is a microRNA suppressing the expression of the human TDP-43 gene by targeting the region consisting of nucleotides at positions 2108 to 2114 (CAAUGCA) in the 3'-UTR sequence of the gene.

[Example 2] Variation of Human miR-33 Nucleotide Sequence as TDP-43 Expression Suppressor As mentioned above, the microRNA causes the degradation or translational inhibition of the mRNA of a target gene by imperfect pairing with the mRNA. The pattern of this pairing varies depending on the combinations of microRNAs and target mRNAs. Typically, a microRNA functions by the perfect pairing of the seed sequence moiety at positions 2 to 8 counted from the 5' end of the microRNA with the target mRNA and the partial pairing of a 3' region downstream from the seed sequence with the target mRNA. Accordingly, the introduction of some mutations (base substitution, deletion, insertion, etc.) to a sequence other than the seed sequence often does not impair functions as a suppressor of the expression of the target gene. Some microRNAs are known to function even after substitution of a portion of the seed sequence (e.g., Japanese Patent No. 5149528).

Thus, study was made on an acceptable change in the sequence of the human miR-33 functioning as a TDP-43 expression suppressor.

Figure 2A:
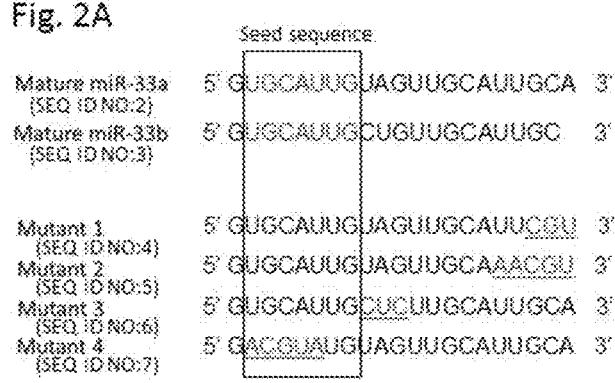
FIG. 2A shows the sequences of miR-33a and miR-33b, both of which are guide RNAs, and the sequences of variants of miR-33a (Mutant 1-4), in which a part of the sequence is substituted and differs from the sequence of miR-33a. In each variant, the seed sequence of miR-33 is boxed and the position of the mutation is underlined.

FIG. 2A shows the nucleotide sequences of miR-33a and miR-33b. When these microRNAs are compared, miR-33b differs in that bases at positions 9 and 10 counted from the 5' end of miR-33a are substituted and one 3'-terminal base is deleted.

On the basis of the nucleotide sequence of this miR-33a, variant microRNAs (3 types) were designed such that 3' bases downstream from the seed sequence were substituted. Specifically these variants were Mutant 1 (SEQ ID NO: 4) obtained by the substitution of three 3'-terminal bases of miR-33a, Mutant 2 (SEQ ID NO: 5) obtained by the substitution of five 3'-terminal bases, and Mutant 3 (SEQ ID NO: 6) obtained by the substitution of three bases 3'-adjacent to the seed sequence. In addition, Mutant 4 (SEQ ID NO: 7) was also prepared by the substitution of 5 bases within the seed sequence.

Figure 2B:
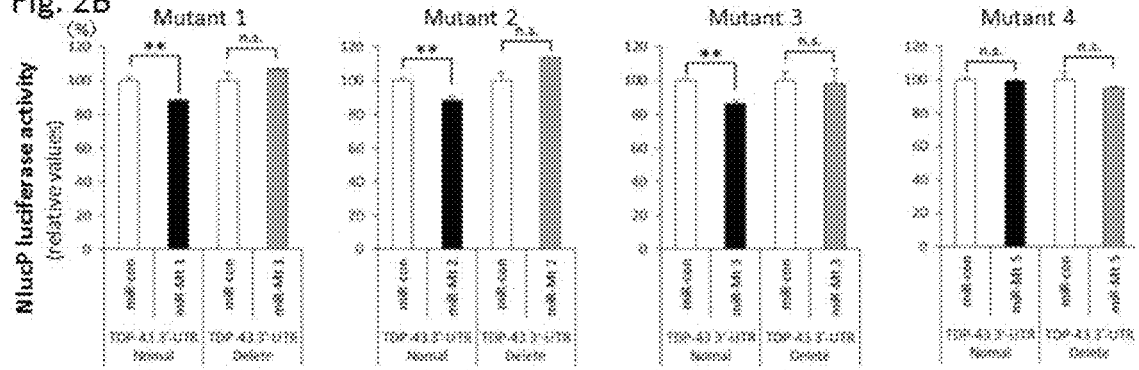
FIG. 2B shows the results of luciferase reporter assay of the HEK293T cells at 48 hours after the cells were transfected with either a miR-33a variant expression plasmid encoding any one of the Mutant 1 to 4 shown in FIG. 2A, or a miR-con expression plasmid. Prior to the infection, one of the reporter genes (i.e., Normal or Del 1+2) and the internal control gene shown in FIG. 1D had been introduced into the HEK293T cells.

These 4 types of variant microRNAs were subjected to 3'UTR luciferase reporter assay using the Normal or Del1+2 reporter gene (Procedure 1). The results are shown in FIG. 2B.

Mutants 1 to 3 expressed in the cells harboring Normal significantly reduced the NlucP luciferase activity, whereas Mutants 1 to 3 expressed in the cells harboring Del1+2 did not change the activity. Accordingly, it was shown that even if up to five 3' bases downstream from the seed sequence are substituted, the resulting miR-33a maintains the activity suppressing the expression of TDP-43 mRNA by acting on the 3'UTR of the mRNA.

By contrast, neither Mutant 4 expressed in the cells harboring Del1+2 nor Mutant 4 expressed in the cells harboring Normal influenced the NlucP luciferase activity. Accordingly, it was shown that by the substitution of bases within the seed sequence, miR-33a loses the activity of suppressing the expression of a gene having the 3'UTR of the TDP-43 gene as UTR.

The results described above demonstrated that the human miR-33 does not lose the function of suppressing the expression of the TDP-43 gene even if up to five 3' nucleotides downstream from the seed sequence are changed (by base substitution, deletion, or insertion).

[Example 3] Regulation of Expression of miR-33 Family by TDP-43

TDP-43 is known to promote the process of forming pre-miRNA from pri-miRNA and/or the process of forming a double-stranded mature miRNA from pre-miRNA for certain microRNAs (Kawahara Y. and Mieda-Sato A., Proc. Natl. Acad. Sci. USA, 109: 3347-3352, 2012). Thus, an experimental system given below was prepared to analyze the influence of the expression level of TDP-43 on the expression level of human miR-33.

The present inventors analyzed the expression levels of miR-33a and miR-33b in human healthy individual-derived iPSC, neurons differentiation-induced from the human healthy individual-derived iPSC, and human cerebrospinal samples according to Procedure 5 and consequently revealed that the expression level of miR-33b is very small (level difficult to detect); thus miR-33b is not substantially expressed in these cells or tissues. Accordingly, only miR-33a was analyzed as the human miR-33 in the subsequent analysis.

<TDP-43 Overexpression in Cultured Cell>

Figure 3A:
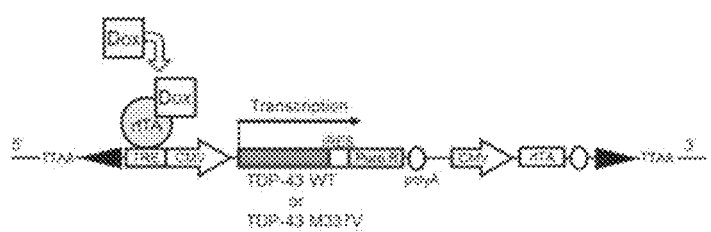
FIG. 3A shows a schematic view of the construct which expresses human TDP-43 protein (wild-type or M337V variant) under the control of tetracycline-inducible promoter (i.e., a CMV minimal promoter having a tetracycline-responsive element (TRE) consisting of seven consecutive tetO sequences). In the view, 2 black triangles represent the target sequences of piggyBac transposase (i.e., inverted terminal repeat sequences).

A construct expressing human TDP-43 protein (wild-type or M337V variant) under the control of tetracycline-inducible promoter (FIG. 3A) was prepared and transferred to HEK293T cells to prepare a stable expression line. Hereinafter, the stable expression line harboring the construct encoding the wild-type or M337V variant TDP-43 is referred to as WT TDP-43-transfected cells or M337V TDP-43-transfected cells.

Figure 3B:
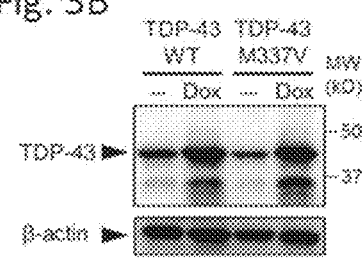
FIGS. 3B and 3C show the results of measuring the TDP-43 protein level (FIG. 3B) and the miR-33a level (FIG. 3C) of the stable expression line of HEK293T cells (WT TDP-43-introduced cells or M337V TDP-43-introduced cells), into which the construct shown in FIG. 3A had been introduced, at 48 hours after DOX was added to the culture medium (n=3, mean±standard error).
Figure 3C:
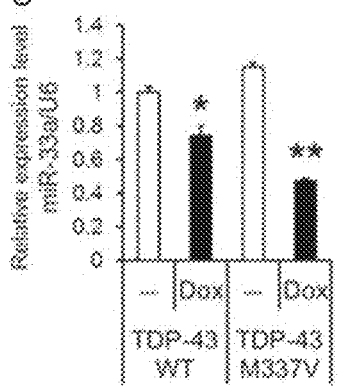

Doxycycline (hereinafter, abbreviated to DOX; final concentration: 1 µg/ml) was added to media containing these 2 types of stable expression lines to induce the expression of TDP-43. Results of measuring the TDP-43 protein level (FIG. 3B) and the miR-33a level (FIG. 3C) 48 hours after the DOX addition are shown. Both of the WT TDP-43-transfected cells and the M337V TDP-43-transfected cells exhibited marked increase in TDP-43 protein level (FIG. 3B) and significant decrease in miR-33a level (FIG. 3C) in the DOX addition groups. Specifically, the miR-33a expression level was decreased to approximately 74% in the WT TDP-43-transfected cells and approximately 63% in the M337V TDP-43-transfected cells, as compared with the miR-33a expression level in the DOX non-addition groups. No significant change in miR-33a expression level was observed in a stable expression line harboring a construct encoding DAP-LYAR protein (Ly-1 antibody reactive clone, DNA-binding protein) instead of the TDP-43 protein, even when the expression of LYAR was induced by the addition of DOX (data not shown).

These results indicate that the expression level of miR-33a is lowered as the TDP-43 protein level is increased, and suggest the possibility that the expression of miR-33a is suppressed directly or indirectly by the TDP-43 protein. Thus, the presence or absence of the direct interaction between the TDP-43 protein and miR-33a was examined by use of the RNA immunoprecipitation (RIP) method.

Figure 3D:
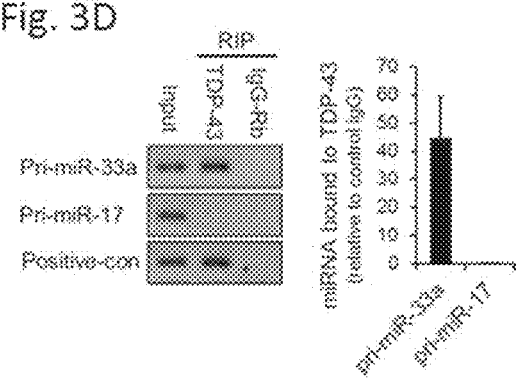
FIG. 3D shows the result of analyzing RNAs which was immunoprecipitated with anti-TDP-43 antibody or normal mouse IgG due to its binding thereto, using the cell lysate prepared from the DOX-treated WT TDP-43-transfected cells shown in FIG. 3B. Left panel shows the result (a gel image) of electrophoresis of the PCR products which were amplified from the immunoprecipitated fraction using Pri-miR-33a primer set or Pri-miR-17 primer set. Right panel shows the result of analyzing the amount (signal) of PCR represents amplified using the Pri-miR-33a primer set.

A cell lysate ($5\times10^7$ cells/150 µl RIP lysis buffer) was prepared from the DOX-treated WT TDP-43-transfected cells using EZ-Magna RIP Kit (manufactured by Merck Millipore). An anti-TDP-43 antibody (manufactured by ProteinTech Group, 7.5 µg) or normal mouse IgG (10 µg) bound with magnetic beads were added to the cell lysate, which was then incubated overnight at 4° C. The beads were recovered (=immunoprecipitated fraction), and qRT-PCR and end-point RT-PCR were carried out by the addition of a pri-miR-33a primer set (SEQ ID NOs: 31 and 32) to analyze the presence or absence of a PCR product (FIG. 3D). As shown in FIG. 3D, the immunoprecipitated fraction based on the anti-TDP-43 antibody yielded a product amplified with the pri-miR-33a primer set, but yielded no product amplified with a pri-miR-17 primer set (SEQ ID NOs: 33 and 34).

These results indicate that the immunoprecipitated fraction of the anti-TDP-43 antibody contained pri-miR-33a, and suggests that TDP-43 and pri-miR-33a were specifically bound in the cell lysate.

The results described above demonstrated that the TDP-43 protein is capable of directly regulating (specifically, suppressing) the expression of miR-33a by binding to pri-miR-33a.

<TDP-43 Knockout in Human Neuron>

Next, an attempt was made to analyze the influence of decrease in TDP-43 expression level on the expression of miR-33a using human neurons. For this purpose, a human iPSC line functionally lacking the TDP-43 gene (TDP-43 knockout human iPSC line; also referred to as TDP-43 KO iPSC) was prepared using the Transcription Activator-Like Effector Nuclease (TALEN) system. This system is based on a method which involves using TALEN having an engineered DNA-binding sequence to introduce a double-stranded DNA break to an arbitrary position on the genome and introducing a mutation such as deletion, substitution, or insertion to the arbitrary site on the genome through the use of the reaction of repairing the DNA break by homologous recombination with a foreign DNA (donor plasmid 1 in the present method) (Miller J. C., et al., Nat. Biotechnol., 29: 143-148, 2011).

Figure 4B:
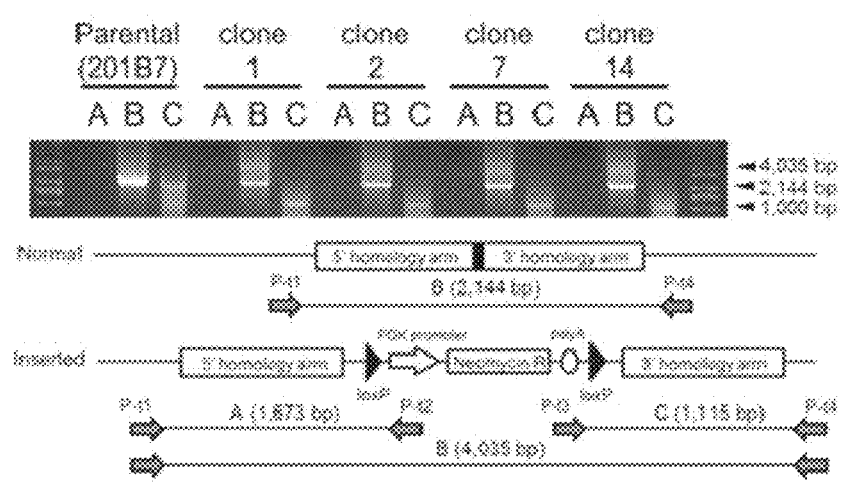
FIG. 4B shows the result of analyzing the products of genomic PCR which was carried out for the neomycin-resistant clones (Clones 1, 2, 7, and 14) using 3 primer sets (A-C). The primer set B yields 4,035-bp PCR product from the clone in which the neomycin selection cassette has been inserted into the exon 2 of the TDP-43 gene. On the other hand, the primer set B yields 2,144-bp PCR product from the clone in which the neomycin selection cassette has not been inserted.
Figure 4C:
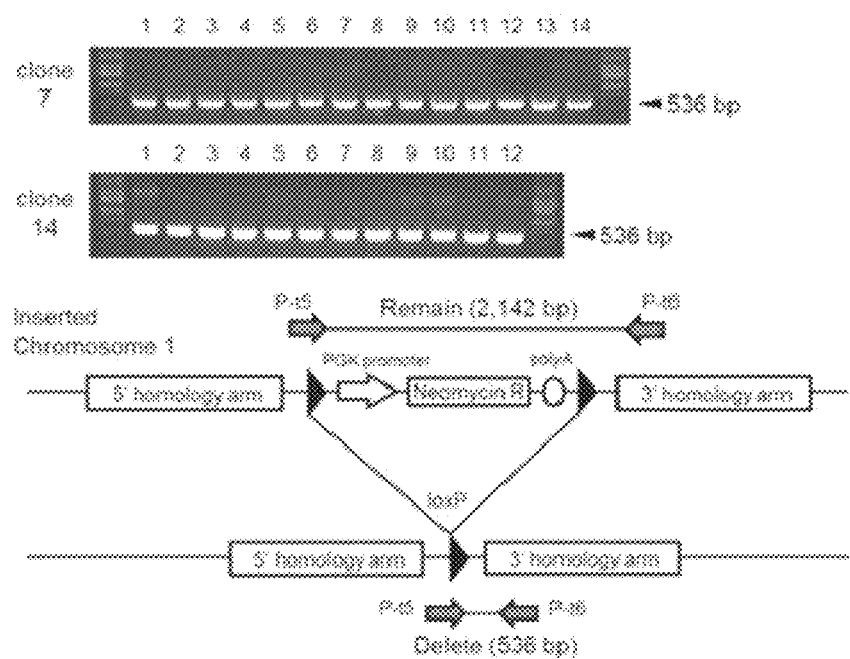
FIG. 4C shows the result of genomic PCR carried out for the clones 7 and 14 using P-t5/P-t6 primer set. Prior to the PCR, both clones were allowed to express Cre recombinase. The clone in which the cassette has been removed yields a 536-bp PCR product, whereas the clone keeping the cassette yields a 2,142-bp PCR product.
Figure 4D:
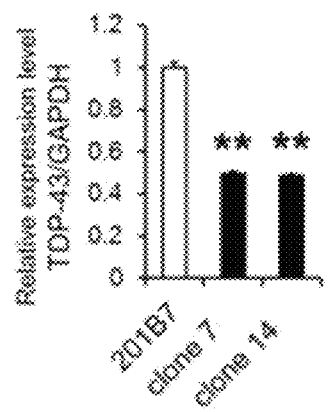
FIG. 4D shows the result of analyzing the level of TDP-43 mRNA in the clones 7 and 14.
Figure 4E:
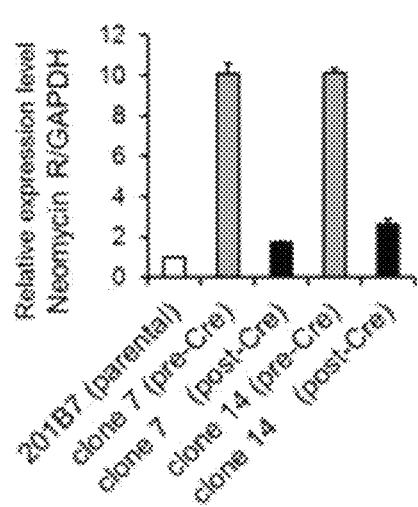
FIG. 4E shows the result of measuring the expression level of neomycin-resistant gene (the amount of mRNA) in the clones 7 and 14 before and after allowing the expression of Cre recombinase.

This Procedure is summarized in FIG. 4A. TALEN-L and TALEN-R respectively binding to regions upstream (TDP-43 KO TALEN-L; SEQ ID NO: 15) and downstream (TDP-43 KO TALEN-R; SEQ ID NO: 16) of the start codon present in exon 2 of TDP-43 were designed. Expression vectors encoding these 2 types of TALENs were transferred, together with donor plasmid 1 (construct in which the homologous arms of TDP-43 gene sequences were located upstream and downstream of a neomycin selection cassette having loxP sequences at both ends; see Procedure 2), to normal human-derived 201B7 iPSC. Then, genomic PCR was carried out using various primers (TDP-43 KO P-t1 to TDP-43 KO P-t4; SEQ NOs: 23 to 26) to select cells having an insert of a portion (i.e., the neomycin selection cassette) of the donor plasmid 1 in the neighborhood of the start codon of the TDP-43 gene (clones 1, 2, 7, and 14 in FIG. 4B). These 4 clones were allowed to express Cre recombinase. Then, genomic PCR was carried out using TDP-43 KO P-t5 (SEQ ID NO: 27) and TDP-43 KO P-t6 (SEQ ID NO: 28) to select clones free from the selection cassette in the neighborhood of the start codon of the TDP-43 gene (clones 7 and 14 in FIG. 4C). These clones were also confirmed to express no neomycin-resistant gene (FIG. 4E). The clones 7 and 14 were sequenced to confirm that the cassette was removed and the full-length TDP-43 exon 2 in one of the alleles was deleted. The procedures for the preparation of the donor plasmid 1, the gene transfer, the selection of transfected cells, and the removal of the selection cassette by Cre recombinase, etc., abided by Procedure 2.

Figure 4F:
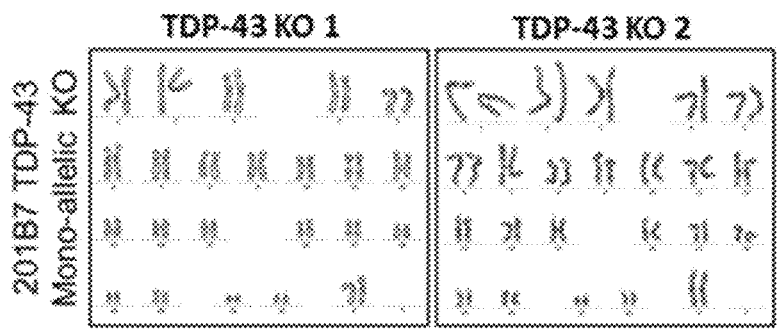
FIG. 4F shows the result of karyotype analysis for the clones 7 (TDP-43 KO 1) and 14 (TDP-43 KO 2), both of which were confirmed that the selection cassette had been removed.

Accordingly, 2 clones (clones 7 and 14) were obtained as monoallelic TDP-43 KO iPSC lines. Hereinafter, these clones 7 and 14 are referred to as "TDP-43 KO 1" and "TDP-43 KO 2", respectively. The TDP-43 KO 1 and the TDP-43 KO 2 both had normal karyotype (46+XX) as a result of karyotype analysis (FIG. 4F). Also, the expression level of TDP-43 in these clones was decreased to approximately half the expression level of TDP-43 in the parent line (201B7) (FIG. 4D).

Subsequently, neurons were differentiation-induced from the TDP-43 KO iPSC by use of SFEBq according to Procedure 3. Hereinafter, the cells differentiation-induced from TDP-43 KO 1 and TDP-43 KO 2 are referred to as "TDP-43 KO1-N" and "TDP-43 KO2-N", respectively.

Figure 5A:
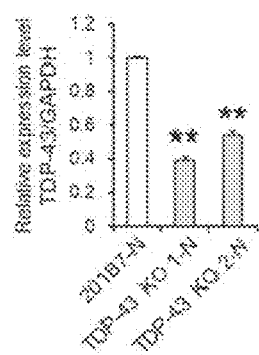
FIG. 5A-E show the results of measuring the TDP-4 mRNA level (FIG. 5A), the TDP-43 protein level (FIGS. 5B and 5C), the expression level of miR-33a (FIG. 5D), and the intracellular cholesterol level (FIG. 5E) of the neuron (N) which was induced from 201B7, TDP-43 KO 1 (the clone 7), or TDP-43 KO 2 (the clone 14) to differentiate into a neuron (n=3, mean±SEM, respectively).
Figure 5B:
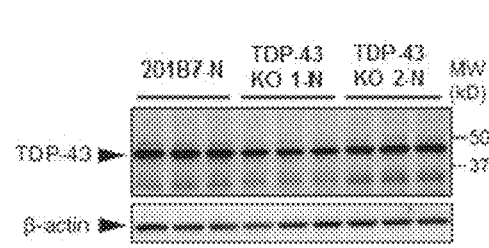
Figure 5C:
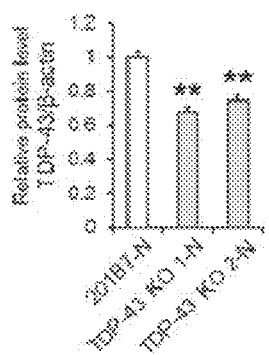

50 days after the differentiation induction (i.e., on Day 50), the TDP-4 mRNA level (FIG. 5A), the TDP-43 protein level (FIGS. 5B and 5C), the expression level of miR-33a (FIG. 5D), and the intracellular cholesterol level (FIG. 5E) were measured in these TDP-43 KO-N cells. The TDP-43 mRNA level of TDP-43 KO-N was approximately half the level in the neurons (201B7-N) differentiated from the parent line (specifically, approximately 39% in TDP-43 KO1-N and approximately 56% in TDP-43 KO2-N; FIG. 5A), and the TDP-43 protein level was also remarkably decreased (approximately 65% in TDP-43 KO1-N and approximately 74% in TDP-43 KO2-N; FIG. 5C).

Accordingly, it was demonstrated that the TDP-43 KO iPSC lines maintain the low expression level of TDP-43 even after being differentiated into neurons.

Figure 5D:
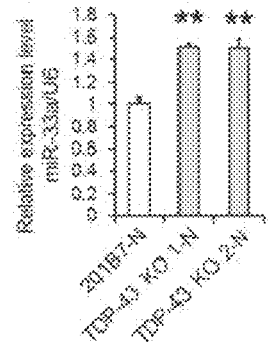
Figure 5E:
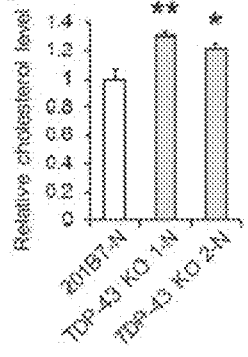

By contrast, the expression level of miR-33a was significantly increased in TDP-43 KO-N (approximately 150% in TDP-43 KO1-N and approximately 144% in TDP-43 KO2-N with respect to 201B7-N; FIG. 5D), and the intracellular cholesterol level was also significantly increased (approximately 127% in TDP-43 KO1-N and approximately 120% in TDP-43 KO2-N with respect to 201B7-N; FIG. 5E). In short, it was revealed that in human neurons, the expression level of miR-33a is increased and intracellular reaction regulated by miR-33a is enhanced (the expression level of functional miR-33a is increased), as the expression level of TDP-43 is decreased.

The results described above demonstrated that TDP-43 also negatively regulates the expression of miR-33a in human neurons and the TDP-43 protein level and the miR-33a level inversely correlate with each other in neurons.

<Expression Level of miR-33a in Mouse Model of TDP-43 Proteinopathy and TDP-43 Proteinopathy Patient-Derived iPSC>

The results described above suggest the possibility that the expression of miR-33a is suppressed in cells with overexpressed TDP-43. Thus, the expression level of miR-33a was analyzed in mouse models of TDP-43 proteinopathy and TDP-43 proteinopathy patient-derived iPSC.

Figure 6A:
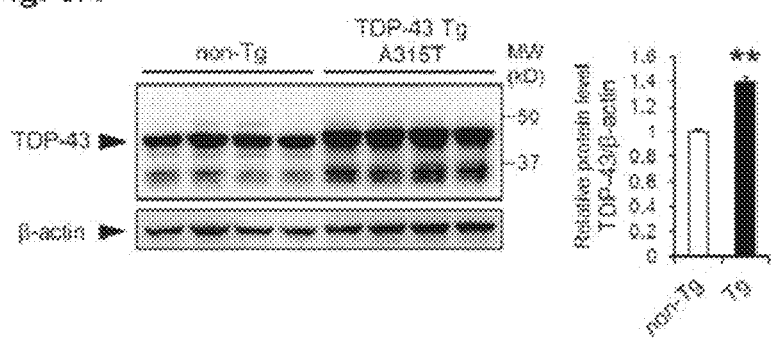
FIGS. 6A and B show the results of measuring the TDP-4 protein level (FIG. 6A) and the miR-33a level (FIG. 6B) in the spinal cords dissected from 4-month-old transgenic mice harboring a human A315T variant TDP-43 gene (TDP-43 Tg A315T) or non-transgenic litermates thereof (non-Tg).
Figure 6B:
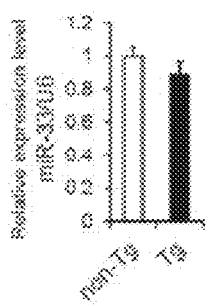
FIG. 6C shows the result of analyzing the expression level of miR-33a in the iPSC lines (201B7, TIG107, N117113) established from healthy individuals and the iPSC lines (A21428 line, ND32947E9 line) established from ALS patients having a mutation in the TDP-43 gene (Q343R or G298S mutation) (n=3, mean±SEM).
FIG. 6D depicts a relationship between TDP-43 and miR-33a in a human neuron. Right panel represents an equilibrium state where TDP-43 protein and miR-33a suppress each other's expression and thereby, their expression levels are balanced (Normal condition). Light panel represents a state where the expression level of TDP-43 became predominant as a result of losing the balance (TDP-43 proteinopathy).

The mouse models of TDP-43 proteinopathy used were transgenic mice harboring a human A315T variant TDP-43 gene placed under the control of mouse prion promoter (stock number: 010700, available from The Jackson Laboratory) (Wegorzewska I., et al., Proc. Natl. Acad. Sci. USA, 106: 18809-18814, 2009). As shown in FIG. 6A, the TDP-43 protein is overexpressed in the spinal cord tissues of the mice. As a result of analyzing the miR-33 level in the spinal cord tissues, a tendency of a lower level than that in control mice (non-transgenic littermates) was confirmed (FIG. 6B).

Figure 6C:
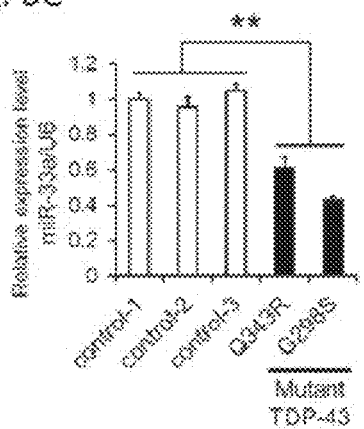

Next, the expression level of miR-33a was compared between iPSC lines established from ALS patients having TDP-43 gene mutations and healthy individuals. The 201B7, TIG107, and NI17113 lines were established as healthy individual-derived iPSC, and the A21428 and ND32947E9 lines were established as ALS patient-derived iPSC having the Q343R and G298S variant TDP-43 genes, respectively (Egawa N., et al., Science Translational Medicine, 4: 145ra104, 2012). As shown in FIG. 6C, these patient-derived iPSC lines were found to have a significantly smaller miR-33a level than that of the healthy individual-derived iPSC.

These results strongly suggested that in TDP-43 proteinopathy, the expression level of miR-33 is decreased due to the overexpression of the TDP-43 protein.

Figure 6D:
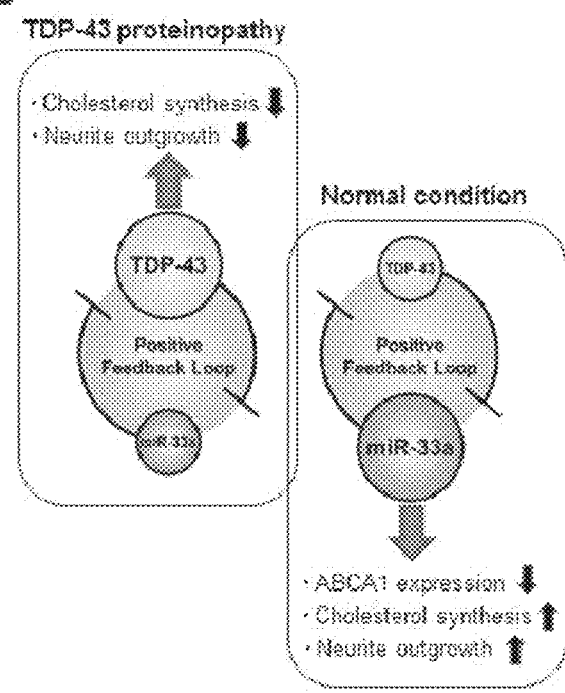

As mentioned above, the TDP-43 protein and miR-33a can mutually suppress the expression directly. Therefore, their expression levels are usually in excellent equilibrium (right panel in FIG. 6D). Such an equilibrium system largely loses the balance as one of the expression levels becomes predominant due to some factor. Thus, it seems difficult to spontaneously restore the initial equilibrium.

The results shown in FIG. 6C strongly suggest the possibility that in TDP-43 proteinopathy patients, the TDP-43 protein becomes predominant due to the imbalance between the expression levels of the TDP-43 protein and miR-33a (left panel in FIG. 6D), resulting in the impaired mechanism underlying the suppression of TDP-43 expression by miR-33a. Thus, a human iPSC line functionally lacking the miR-33a gene was prepared to analyze the influence of the deletion of miR-33a expression from human motor neurons.

[Example 4] Preparation of miR-33a-Knockout Human iPSC miR-33-knockout human iPSC (hereinafter, also referred to as "miR-33a KO iPSC") was prepared using the CRISPR-Cas9 system. This system is based on a method which involves introducing a mutation such as deletion, substitution, or insertion to an arbitrary site on the genome through the use of the reaction where a complex of Cas9 endonuclease and an RNA (i.e., a guide RNA for Cas9) introduces a double strand break to a particular site in the genomic DNA in a manner dependent on the sequence of the guide RNA, and the reaction where the DNA break is repaired by homologous recombination with a foreign DNA (donor plasmid 2 in the present method) (Gaj T., et al., Trends Biotechnol., 31:397-405, 2013; and Doudna J. A., et al., Science, 346, no. 6213, 2014).

Figure 7A:
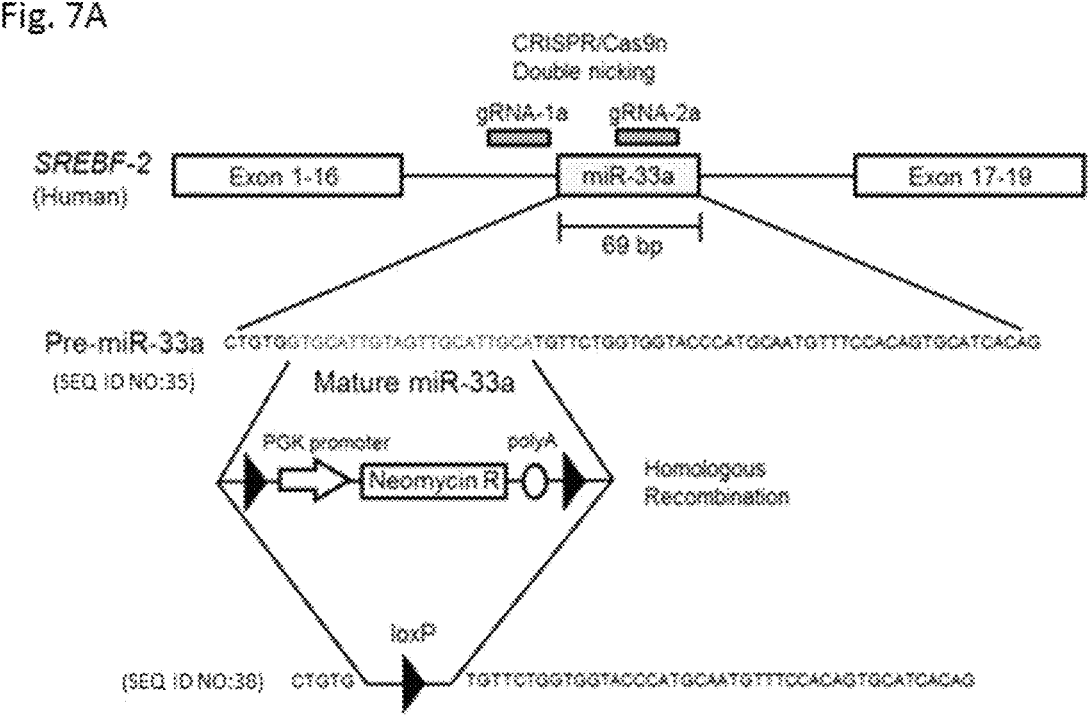
FIG. 7A shows a schematic view of the procedure for generating a human iPSC line (miR-33a KO iPSC), in which miR-33a gene has been knocked out. The nucleotide sequence shown in the bottom part of the figure represents the nucleotide sequence of the neomycin-resistant clone, in which a donor plasmid 2-derived selection cassette had been introduced but, subsequently, the cassette were removed by Cre recombinase.

The procedure is summarized in FIG. 7A (Procedure 2). Expression plasmids for guide RNAs targeting the neighborhood of the seed sequence of miR-33a (miR-33a KO gRNA-1a and -2a; SEQ ID NOs: 12 and 13), a Cas9 endonuclease expression plasmid, and donor plasmid 2 were transferred to 201B7 iPSC to obtain 21 neomycin resistance clones. These clones were subjected to genomic PCR to obtain, from 5 clones (clones 8, 9, 14, 15, and 18), PCR products (3,398-bp DNA fragments amplified with primer set B) having an insert of a portion (i.e., the neomycin selection cassette) of the donor plasmid 2 in the neighborhood of the seed sequence of the miR-33a gene (FIG. 7B). As a result of quantitative PCR, these clones were confirmed to each have only one copy of the selection cassette insert in their genomes. Then, these 5 clones were allowed to express Cre recombinase to obtain clones free from the selection cassette (FIG. 7D).

Figure 7C:
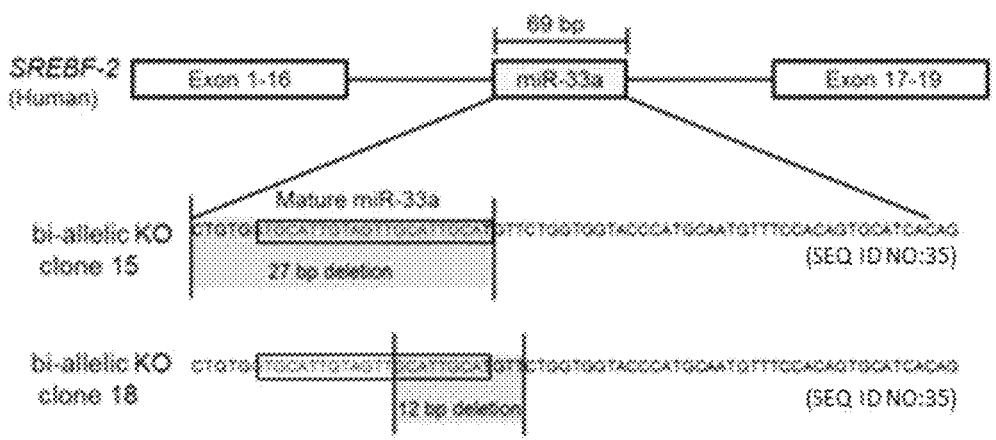
FIG. 7C shows the result of sequencing of the nucleotide of miR-33a gene in the clones 15 and 18, and describes the nucleotide sequence deleted in each clone.

The miR-33a gene and its neighborhood in the 5 clones free from the selection cassette were sequenced. As a result, the clones 15 and 18 were confirmed to lack the nucleotide sequence encoding mature miR-33a in both of the alleles. Specifically, the clone 15 lacked 27 bases (nucleotides) consisting of the whole nucleotide sequence corresponding to mature miR-33a and 5 bases upstream thereof. The clone 18 lacked 12 bases (nucleotides) consisting of eight 3'-terminal bases of the nucleotide sequence corresponding to mature miR-33a and 4 bases downstream thereof (FIG. 7C). Also, the clones 8, 9, and 14 were confirmed to lack the sequence encoding mature miR-33a in only one of the alleles.

Figure 7E:
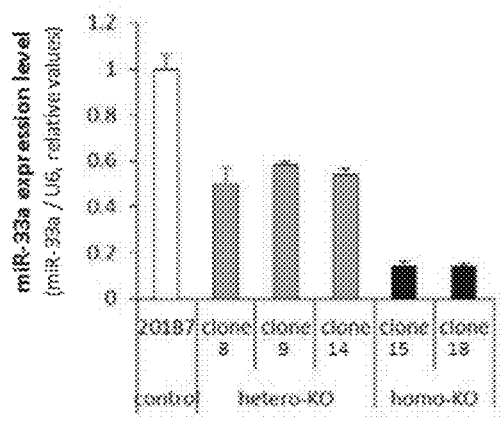
FIG. 7E shows the result of measuring the expression level of miR-33a in 5 miR-33a KO iPSC.

Results of analyzing the expression level of miR-33a in these 5 clones are shown in FIG. 7E. As is evident, the expression level of miR-33a in the clones monoallelically lacking miR-33a (clones 8, 9, and 14) was decreased to almost half the expression level in the parent line (201B7 line), and miR-33a disappeared in the clones biallelically lacking miR-33a (clones 15 and 18).

Figure 7F:
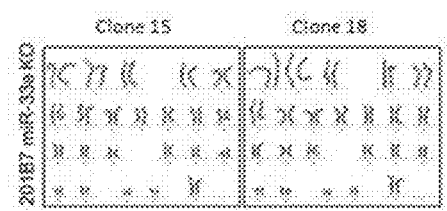
FIG. 7F shows the result of karyotype analysis for the clones 15 and 18.

The 5 clones were further confirmed to have normal karyotype (46+XX) by karyotype analysis (FIG. 7F). Total RNA was extracted from each of the 5 clones to confirm that normal SREBP-2 mRNA was produced by the splicing out of intron 16 (i.e., this genome engineering had no influence on the splicing of SREBP-2 mRNA).

Accordingly, clones 8, 9, and 14 were obtained as monoallelic miR-33a KO iPSC lines, and clone 15 (the full-length mature miR-33 sequence was deleted; hereinafter, referred to as "miR-33a KO 1") and clone 18 (approximately 40% of the mature miR-33 sequence was deleted; hereinafter, referred to as "miR-33a KO 2") were obtained as biallelic miR-33a KO iPSC lines.

[Example 5] Vulnerability of Human iPSC-Derived Motor Neuron Caused by Disappearance of miR-33a Expression and Recovery from the Vulnerability by Transfer of miR-33a A pure culture of motor neurons was prepared from the biallelic miR-33a KO iPSC lines and analyzed for the influence of the disappearance of miR-33a expression on human motor neurons.

MN was differentiation-induced from each of the miR-33a KO 1, the miR-33a KO 2, and 201B7 (Procedure 3), and the cells differentiated into MN were separated by use of FACS (Procedure 4) to prepare a pure culture of MN. Hereinafter, the MN cells obtained by this method from 201B7, miR-33a KO 1, and miR-33a KO 2 are referred to as "201B7-MN", "miR-33a KO 1-MN", and "miR-33a KO 2-MN", respectively.

Figure 8A:
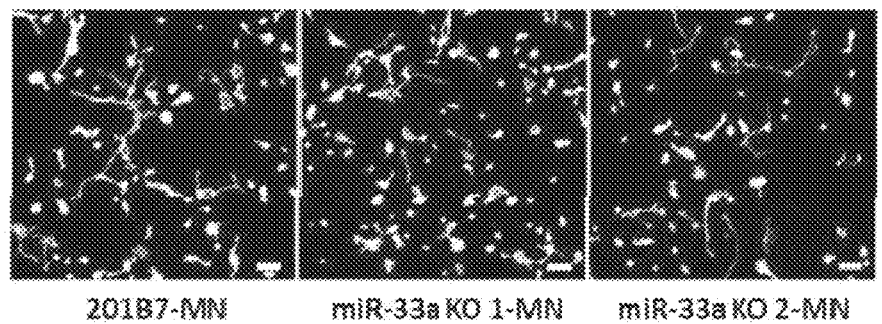
FIG. 8A shows the images of fluorescence microscopy of a pure culture of the motor neuron (MN) which was induced from 201B7, miR-33a KO 1 (clone 1), or miR-33a KO 2 (clone 18) to differentiate into a motor neuron.
Figure 8B:
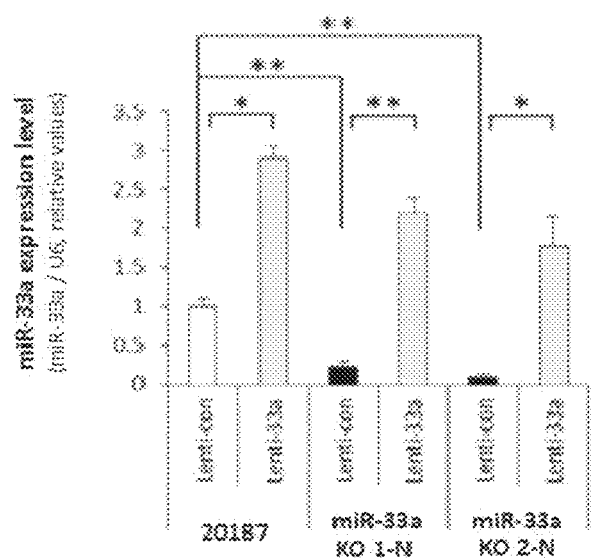
FIGS. 8B, C, and E show the results of measuring the expression level of miR-33a (FIG. 8B), the TDP-43 protein level (FIG. 8C), and the intracellular cholesterol level (FIG. 8E) of the neuron (N) which was induced from 201B7, miR-33a KO 1 (clone 15), or miR-33a KO 2 (clone 18) to differentiate into a neuron (n=3, mean±SEM, respectively). Prior to the measurements, the neuron in the pure culture was infected with either the H1::miR-33a Lenti or the H1::miR-con Lenti. The measurements were carried out on Day 9 after the infection.
Figure 8D:
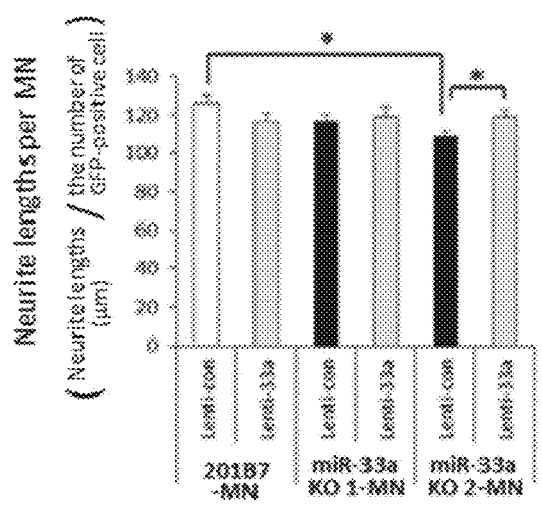
FIG. 8D shows the result of measuring neurite lengths of the motor neurons in the MN pure culture shown in FIG. 8A on Day 9 after the infection of either the H1::miR-33a Lenti or the H1::miR-con Lenti (n=3, mean±SEM, respectively).

The GFP fluorescence microscope photograph of each MN is shown in FIG. 8A. As is evident from the photograph, miR-33a KO 1-MN compared with 201B7-MN tended to have weaker neurites, and miR-33a KO 2-MN compared with 201B7-MN tended to have fewer neurites.

miR-33a was supplied to these iPSC-MN cells using the lentivirus vector to analyze change in neurite length. Results of infecting the cells with the H1::miR-33a Lenti or the H1::miR-con Lenti 36 days after the differentiation induction (i.e., on Day 36) and measuring neurite lengths on Day 45 are shown in FIG. 8D. First, as is evident from the comparison among the H1::miR-con Lenti infection groups, miR-33a KO 1-MN tended to have a shorter neurite length than that of 201B7-MN, and miR-33a KO 2-MN had a significantly shorter neurite length than that of 201B7-MN. Poor neurite outgrowth is pathological properties commonly found in almost all of TDP-43 proteinopathy patient-derived iPSC-MN cells (National Publication of International Patent Application No. 2015-506905; and Egawa N., et al., Science Translational Medicine, 4: 145ra104, 2012).

Next, the neurite lengths of the H1::miR-33a Lenti infection group and the H1::miR-con Lenti infection group of each iPSC-MN were compared to focus on the relationship between the presence or absence of miR-33a and the neurite lengths.

As a result, miR-33a KO 1-MN had longer neurites in the H1::miR-33a Lenti infection group than in the H1::miR-con Lenti infection group, showing a tendency of recovery from neurite vulnerability by the supply of miR-33a. Furthermore, miR-33a KO 2-MN had a significantly larger neurite length in the H1::miR-33a Lenti infection group than in the H1::miR-con Lenti infection group, demonstrating that the supply of miR-33a allows the neurons to recover from poor neurite outgrowth to the same level as in 201B7-MN (FIG. 8D).

Accordingly, it was shown that the disappearance of miR-33a expression in human motor neurons results in pathological neurites.

Next, a culture system of neurons was prepared from each of the miR-33a KO 1, the miR-33a KO 2, and 201B7 to analyze the relationship between miR-33a and TDP-43 protein levels (these neurons are referred to as "miR-33a KO 1-N", "miR-33a KO 2-N", and "201B7-N", respectively).

36 days after the differentiation induction (i.e. on Day 36), the cells were infected with the H1::miR-33a Lenti or the H1::miR-con Lenti. On Day 50, the miR-33a level (FIG. 8B) and the TDP-43 protein level (FIG. 8C) were measured. First, as is evident from the comparison among the H1::miR-con Lenti infection groups, the TDP-43 protein level was significantly increased in miR-33a KO-N. Specifically, the TDP-43 protein level was increased to approximately 130% in miR-33a KO 1-N and approximately 140% in miR-33a KO 2-N, as compared with 201B7-N.

Subsequently, as is evident from the comparison between the H1::miR-33a Lenti infection group and the H1::miR-con Lenti infection group of each iPSC-N, the TDP-43 protein level in all of the iPSC-N cells was significantly decreased by the infection with H1::miR-33a Lenti. Specifically, the TDP-43 protein level was decreased to approximately 70% in 201B7-N, approximately 73% in miR-33a KO 1-N, and approximately 50% in miR-33a KO 2-N.

Accordingly, it was shown that the TDP-43 protein level in human neurons was negatively regulated by miR-33a.

Figure 8E:
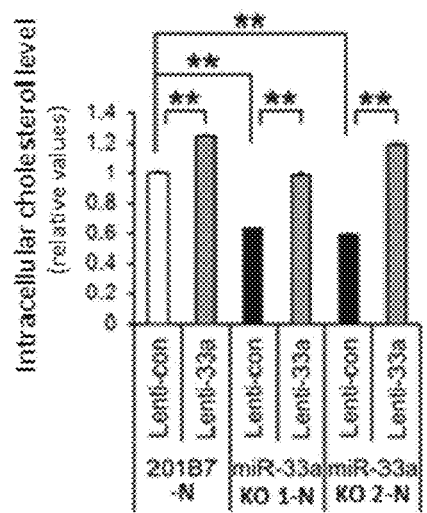

As a result of further measuring the intracellular cholesterol level in these iPSC-N cells, the intracellular cholesterol level was confirmed to vary in conjunction with the expression level of miR-33a (FIG. 8E).

The results described above demonstrated that miR-33 is an important modulator that regulates the TDP-43 protein level in human neurons and the decreased expression of miR-33 in human neurons increases the TDP-43 protein level to create a pathological condition. The results further demonstrated that the supply of miR-33 to human neurons overexpressing TDP-43 decreases the expression of TDP-43 and ameliorates the pathological properties caused by the TDP-43 overexpression.

It was thus concluded that the human miR-33 can serve as a prophylactic or therapeutic drug for TDP-43 proteinopathy.

SEQUENCE LISTING

4996(CR0004) Sequence Listing.txt

The invention claimed is:

1. A therapeutic composition for TDP-43 proteinopathy, comprising:
   one or more nucleic acids consisting of isolated nucleic acids encoding RNAs,
   wherein the RNAs are one or more isolated RNAs of following:
   (i) a variant of human miR-33 represented by SEQ ID NO: 6;
   (ii) a variant of human miR-33 represented by SEQ ID NO: 5;
   (iii) a variant of human miR-33 represented by SEQ ID NO: 4; and
   (iv) one selected from a group consisting of a pre-miRNA of (i), a pre-miRNA of (ii) and a pre-miRNA of (iii), wherein each of the pre-miRNA of (i), the pre-miRNA of (ii) and the pre-miRNA of (iii) is composed of 60 to 100 nucleotides,
   wherein each of the pre-miRNA of (i), the pre-miRNA of (ii) and the pre-miRNA of (iii) is a hairpin RNA having a hairpin-shaped structure composed of imperfectly paired stem and loop moieties,
   wherein the stem moiety of the pre-miRNA of (i) comprises the nucleotides represented by SEQ ID NO: 6, the stem moiety of the pre-miRNA of (ii) comprises the nucleotides represented by SEQ ID NO: 5, the stem moiety of the pre-miRNA of (iii) comprises the nucleotides represented by SEQ ID NO: 4, and
   wherein each of the pre-miRNA of (i), the pre-miRNA of (ii) and the pre-miRNA of (iii) is configured to be cleaved by Dicer in a cell to generate a double-stranded miRNA derived from the stem moiety and finally generate one of (i) to (iii), when the each of pre-miRNA of (i), the pre-miRNA of (ii) and the pre-miRNA of (iii) is directly transferred as an RNA molecule to the cell or is expressed in the cell using an expression vector; and (v) a double-stranded miRNA generated from (iv).

2. The therapeutic composition for TDP-43 proteinopathy according to claim 1, wherein the isolated nucleic acids encoding the RNAs are functionally encoded by a virus vector.

3. The therapeutic composition for TDP-43 proteinopathy according to claim 2, wherein the virus vector is a lentivirus vector or an adeno-associated virus vector.

4. The therapeutic composition for TDP-43 proteinopathy according to claim 1, wherein the RNA comprises at least one or more modified nucleotides.

5. The therapeutic composition for TDP-43 proteinopathy according to claim 1, wherein the one or more nucleic acids are encapsulated in nanoparticles.

6. The therapeutic composition for TDP-43 proteinopathy according to claim 1, wherein the TDP-43 proteinopathy is SOD1-unrelated amyotrophic lateral sclerosis and frontotemporal lobar degeneration with ubiquitin inclusions.

7. The therapeutic composition for TDP-43 proteinopathy according to claim 1, wherein the pre-miRNA of (i) is a variant of human pre-miR-33 represented by SEQ ID NO:10, in which nucleotides at positions 6 to 26 counted from the 5' end have been substituted by nucleotides represented by SEQ ID NO: 6.

8. The therapeutic composition for TDP-43 proteinopathy according to claim 1, wherein the pre-miRNA of (ii) is a variant of human pre-miR-33 represented by SEQ ID NO:10, in which nucleotides at positions 6 to 26 counted from the 5' end have been substituted by nucleotides represented by SEQ ID NO: 5.

9. The therapeutic composition for TDP-43 proteinopathy according to claim 1, wherein the pre-miRNA of (iii) is a variant of human pre-miR-33 represented by SEQ ID NO:10, in which nucleotides at positions 6 to 26 counted from the 5' end have been substituted by nucleotides represented by SEQ ID NO: 4.

* * * * *

SEQUENCE LISTING

```
<160> NUMBER OF SEQ ID NOS: 38

<210> SEQ ID NO 1
<211> LENGTH: 21
<212> TYPE: RNA
<213> ORGANISM: Homo sapiens
<220> FEATURE:
<223> OTHER INFORMATION: miR-33
<220> FEATURE:
<221> NAME/KEY: misc_feature
<222> LOCATION: (2)..(8)
<223> OTHER INFORMATION: seed sequence
<220> FEATURE:
<221> NAME/KEY: misc_feature
<222> LOCATION: (9)..(9)
<223> OTHER INFORMATION: y represents u or c
<220> FEATURE:
<221> NAME/KEY: misc_feature
<222> LOCATION: (10)..(10)
<223> OTHER INFORMATION: w represents a or t
<220> FEATURE:
<221> NAME/KEY: misc_feature
<222> LOCATION: (21)..(21)
<223> OTHER INFORMATION: n represents a or no base

<400> SEQUENCE: 1
gugcauugyw guugcauugc n                                              21

<210> SEQ ID NO 2
<211> LENGTH: 21
<212> TYPE: RNA
<213> ORGANISM: Homo sapiens
<220> FEATURE:
<223> OTHER INFORMATION: miR-33a
<220> FEATURE:
<221> NAME/KEY: misc_feature
<222> LOCATION: (2)..(8)
<223> OTHER INFORMATION: seed sequence

<400> SEQUENCE: 2
gugcauugua guugcauugc a                                              21

<210> SEQ ID NO 3
<211> LENGTH: 20
<212> TYPE: RNA
<213> ORGANISM: Homo sapiens
<220> FEATURE:
<223> OTHER INFORMATION: miR-33b
<220> FEATURE:
<221> NAME/KEY: misc_feature
<222> LOCATION: (2)..(8)
<223> OTHER INFORMATION: seed sequence

<400> SEQUENCE: 3
gugcauugcu guugcauugc                                                20

<210> SEQ ID NO 4
<211> LENGTH: 21
<212> TYPE: RNA
```

```
<213> ORGANISM: Artificial Sequence
<220> FEATURE:
<223> OTHER INFORMATION: miR-33a Mutant 1

<400> SEQUENCE: 4
gugcauugua guugcauucg u                                              21

<210> SEQ ID NO 5
<211> LENGTH: 21
<212> TYPE: RNA
<213> ORGANISM: Artificial Sequence
<220> FEATURE:
<223> OTHER INFORMATION: miR-33a Mutant 2

<400> SEQUENCE: 5
gugcauugua guugcaaacg u                                              21

<210> SEQ ID NO 6
<211> LENGTH: 21
<212> TYPE: RNA
<213> ORGANISM: Artificial Sequence
<220> FEATURE:
<223> OTHER INFORMATION: miR-33a Mutant 3

<400> SEQUENCE: 6
gugcauugcu cuugcauugc a                                              21

<210> SEQ ID NO 7
<211> LENGTH: 21
<212> TYPE: RNA
<213> ORGANISM: Artificial Sequence
<220> FEATURE:
<223> OTHER INFORMATION: miR-33a Mutant 4

<400> SEQUENCE: 7
gacguaugua guugcauugc a                                              21

<210> SEQ ID NO 8
<211> LENGTH: 27
<212> TYPE: RNA
<213> ORGANISM: Artificial Sequence
<220> FEATURE:
<223> OTHER INFORMATION: Modified miR-33a guide strand
<220> FEATURE:
<221> NAME/KEY: misc_feature
<222> LOCATION: (4)..(24)
<223> OTHER INFORMATION: phosphorothioated

<400> SEQUENCE: 8
guggugcauu guaguugcau ugcaugu                                        27

<210> SEQ ID NO 9
<211> LENGTH: 27
<212> TYPE: RNA
<213> ORGANISM: Artificial Sequence
<220> FEATURE:
<223> OTHER INFORMATION: Modified miR-33a passenger strand
<220> FEATURE:
<221> NAME/KEY: misc_feature
<222> LOCATION: (1)..(1)
<223> OTHER INFORMATION: cholesterol is conjugated

<400> SEQUENCE: 9
acaugcaaug caacuacaau gcaccac                                        27

<210> SEQ ID NO 10
<211> LENGTH: 69
```

```
<212> TYPE: RNA
<213> ORGANISM: Homo sapiens
<220> FEATURE:
<223> OTHER INFORMATION: pre-miR-33a
<220> FEATURE:
<221> NAME/KEY: misc_feature
<222> LOCATION: (6)..(26)
<223> OTHER INFORMATION: /product=hsa-mir-33a-5p, guide strand
<220> FEATURE:
<221> NAME/KEY: misc_feature
<222> LOCATION: (46)..(67)
<223> OTHER INFORMATION: /product=hsa-mir-33a-3p, passenger strand

<400> SEQUENCE: 10
cuguggugca uuguaguugc auugcauguu cuggugguac ccaugcaaug uuuccacagu      60
gcaucacag                                                             69

<210> SEQ ID NO 11
<211> LENGTH: 96
<212> TYPE: RNA
<213> ORGANISM: Homo sapiens
<220> FEATURE:
<223> OTHER INFORMATION: pre-miR-33b
<220> FEATURE:
<221> NAME/KEY: misc_feature
<222> LOCATION: (16)..(35)
<223> OTHER INFORMATION: /product=hsa-mir-33b-5p, guide strand
<220> FEATURE:
<221> NAME/KEY: misc_feature
<222> LOCATION: (54)..(75)
<223> OTHER INFORMATION: /product=hsa-mir-33b-3p, passenger strand

<400> SEQUENCE: 11
gcgggcggcc ccgcggugca uugcuguugc auugcacgug ugugaggcgg gugcagugcc      60
ucggcagugc agcccggagc cggccccugg caccac                               96

<210> SEQ ID NO 12
<211> LENGTH: 132
<212> TYPE: RNA
<213> ORGANISM: Artificial Sequence
<220> FEATURE:
<223> OTHER INFORMATION: control miR

<400> SEQUENCE: 12
cuggaggcuu gcugaaggcu guaugcugaa auguacugcg cguggagacg uuuuggccac      60
ugacugacgu cuccacgcag uacauuucag gacacaaggc cuguuacuag cacucacaug     120
gaacaaaugg cc                                                         132

<210> SEQ ID NO 13
<211> LENGTH: 23
<212> TYPE: RNA
<213> ORGANISM: Artificial Sequence
<220> FEATURE:
<223> OTHER INFORMATION: miR-33a KO gRNA-1a

<400> SEQUENCE: 13
gcugcccgcc aggagguaug cgg                                             23

<210> SEQ ID NO 14
<211> LENGTH: 23
<212> TYPE: RNA
<213> ORGANISM: Artificial Sequence
<220> FEATURE:
<223> OTHER INFORMATION: miR-33a KO gRNA-2a

<400> SEQUENCE: 14
```

```
uguaguugca uugcauguuc ugg                                          23

<210> SEQ ID NO 15
<211> LENGTH: 18
<212> TYPE: RNA
<213> ORGANISM: Artificial Sequence
<220> FEATURE:
<223> OTHER INFORMATION: TDP-43 KO TALEN-L

<400> SEQUENCE: 15
uuuucucuuu aggaaaag                                                18

<210> SEQ ID NO 16
<211> LENGTH: 18
<212> TYPE: RNA
<213> ORGANISM: Artificial Sequence
<220> FEATURE:
<223> OTHER INFORMATION: TDP-43 KO TALEN-R

<400> SEQUENCE: 16
uauauucggg uaaccgaa                                                18

<210> SEQ ID NO 17
<211> LENGTH: 20
<212> TYPE: DNA
<213> ORGANISM: Artificial Sequence
<220> FEATURE:
<223> OTHER INFORMATION: miR-33a KO P-a1 primer

<400> SEQUENCE: 17
cctgtgtctc tgacttccag                                              20

<210> SEQ ID NO 18
<211> LENGTH: 20
<212> TYPE: DNA
<213> ORGANISM: Artificial Sequence
<220> FEATURE:
<223> OTHER INFORMATION: miR-33a KO P-a2 primer

<400> SEQUENCE: 18
ccagaggcca cttgtgtagc                                              20

<210> SEQ ID NO 19
<211> LENGTH: 20
<212> TYPE: DNA
<213> ORGANISM: Artificial Sequence
<220> FEATURE:
<223> OTHER INFORMATION: miR-33a KO P-a3 primer

<400> SEQUENCE: 19
cttcttgacg agttcttctg                                              20

<210> SEQ ID NO 20
<211> LENGTH: 20
<212> TYPE: DNA
<213> ORGANISM: Artificial Sequence
<220> FEATURE:
<223> OTHER INFORMATION: miR-33a KO P-a4 primer

<400> SEQUENCE: 20
agggtggctg caagcctctc                                              20

<210> SEQ ID NO 21
<211> LENGTH: 20
<212> TYPE: DNA
<213> ORGANISM: Artificial Sequence
```

```
<220> FEATURE:
<223> OTHER INFORMATION: miR-33a KO P-a5 primer

<400> SEQUENCE: 21
ctgtggcgca acgcaattag                                                 20

<210> SEQ ID NO 22
<211> LENGTH: 19
<212> TYPE: DNA
<213> ORGANISM: Artificial Sequence
<220> FEATURE:
<223> OTHER INFORMATION: miR-33a KO P-a6 primer

<400> SEQUENCE: 22
ttcctgggat ggctgtgac                                                  19

<210> SEQ ID NO 23
<211> LENGTH: 20
<212> TYPE: DNA
<213> ORGANISM: Artificial Sequence
<220> FEATURE:
<223> OTHER INFORMATION: TDP-43 KO P-t1 primer

<400> SEQUENCE: 23
ggtgtccctg tcgggcttcc                                                 20

<210> SEQ ID NO 24
<211> LENGTH: 20
<212> TYPE: DNA
<213> ORGANISM: Artificial Sequence
<220> FEATURE:
<223> OTHER INFORMATION: TDP-43 KO P-t2 primer

<400> SEQUENCE: 24
ccagaggcca cttgtgtagc                                                 20

<210> SEQ ID NO 25
<211> LENGTH: 20
<212> TYPE: DNA
<213> ORGANISM: Artificial Sequence
<220> FEATURE:
<223> OTHER INFORMATION: TDP-43 KO P-t3 primer

<400> SEQUENCE: 25
ccgattcgca gcgcatcgcc                                                 20

<210> SEQ ID NO 26
<211> LENGTH: 20
<212> TYPE: DNA
<213> ORGANISM: Artificial Sequence
<220> FEATURE:
<223> OTHER INFORMATION: TDP-43 KO P-t4 primer

<400> SEQUENCE: 26
attctcctgc gtctgcctcc                                                 20

<210> SEQ ID NO 27
<211> LENGTH: 20
<212> TYPE: DNA
<213> ORGANISM: Artificial Sequence
<220> FEATURE:
<223> OTHER INFORMATION: TDP-43 KO P-t5 primer

<400> SEQUENCE: 27
ccatcgcgca acgcaattag                                                 20
```

```
<210> SEQ ID NO 28
<211> LENGTH: 23
<212> TYPE: DNA
<213> ORGANISM: Artificial Sequence
<220> FEATURE:
<223> OTHER INFORMATION: TDP-43 KO P-t6 primer

<400> SEQUENCE: 28
ggcagagaga aggataagac cag                                             23

<210> SEQ ID NO 29
<211> LENGTH: 23
<212> TYPE: DNA
<213> ORGANISM: Artificial Sequence
<220> FEATURE:
<223> OTHER INFORMATION: human TDP-43-Fw primer

<400> SEQUENCE: 29
tgaatatatt cgggtaaccg aag                                             23

<210> SEQ ID NO 30
<211> LENGTH: 20
<212> TYPE: DNA
<213> ORGANISM: Artificial Sequence
<220> FEATURE:
<223> OTHER INFORMATION: human TDP-43-Rv primer

<400> SEQUENCE: 30
ctgtaaccgt ggagagcagc                                                 20

<210> SEQ ID NO 31
<211> LENGTH: 21
<212> TYPE: DNA
<213> ORGANISM: Artificial Sequence
<220> FEATURE:
<223> OTHER INFORMATION: pri-miR-33a RIP-Fw primer

<400> SEQUENCE: 31
ccacagtgca tcacagaggc c                                               21

<210> SEQ ID NO 32
<211> LENGTH: 20
<212> TYPE: DNA
<213> ORGANISM: Artificial Sequence
<220> FEATURE:
<223> OTHER INFORMATION: pri-miR-33a RIP-Rv primer

<400> SEQUENCE: 32
atagggcctt cagtcagggc                                                 20

<210> SEQ ID NO 33
<211> LENGTH: 21
<212> TYPE: DNA
<213> ORGANISM: Artificial Sequence
<220> FEATURE:
<223> OTHER INFORMATION: pri-miR-17 RIP-Fw primer

<400> SEQUENCE: 33
tagcattatg gtgacagctg c                                               21

<210> SEQ ID NO 34
<211> LENGTH: 21
<212> TYPE: DNA
<213> ORGANISM: Artificial Sequence
<220> FEATURE:
<223> OTHER INFORMATION: pri-miR-17 RIP-Rv primer
```

```
<400> SEQUENCE: 34
agcaggccct gcactttaaa g                                             21

<210> SEQ ID NO 35
<211> LENGTH: 69
<212> TYPE: DNA
<213> ORGANISM: Homo sapiens
<220> FEATURE:
<223> OTHER INFORMATION: genomic DNA of pre-miR-33a

<400> SEQUENCE: 35
ctgtggtgca ttgtagttgc attgcatgtt ctggtggtac ccatgcaatg tttccacagt   60
gcatcacag                                                           69

<210> SEQ ID NO 36
<211> LENGTH: 21
<212> TYPE: DNA
<213> ORGANISM: Homo sapiens
<220> FEATURE:
<223> OTHER INFORMATION: genomic DNA of miR-33a

<400> SEQUENCE: 36
gtgcattgta gttgcattgc a                                             21

<210> SEQ ID NO 37
<211> LENGTH: 63
<212> TYPE: DNA
<213> ORGANISM: Homo sapiens
<220> FEATURE:
<223> OTHER INFORMATION: genomic fragment of TDP-43

<400> SEQUENCE: 37
tatctctttt ctctttagga aaagtaaaag atgtctgaat atattcgggt aaccgaagat   60
gag                                                                 63

<210> SEQ ID NO 38
<211> LENGTH: 48
<212> TYPE: DNA
<213> ORGANISM: Homo sapiens
<220> FEATURE:
<223> OTHER INFORMATION: pre-miR-33a mutant

<400> SEQUENCE: 38
ctgtgtgttc tggtggtacc catgcaatgt ttccacagtg catcacag                48
```